United States Patent
Wei et al.

(10) Patent No.: US 11,466,023 B2
(45) Date of Patent: Oct. 11, 2022

(54) COMBINATION OF A MCL-1 INHIBITOR AND A STANDARD OF CARE TREATMENT FOR HEMATOLOGIC CANCERS, USES AND PHARMACEUTICAL COMPOSITIONS THEREOF

(71) Applicants: LES LABORATOIRES SERVIER, Suresnes (FR); NOVARTIS AG, Basel (CH)

(72) Inventors: Andrew Wei, Surrey Hills (AU); Donia Moujalled, Lalor (AU); Giovanna Pomilio, Pascoe Vale (AU); Olivier Geneste, Rueil-Malmaison (FR); Ana Leticia Maragno, Croissy-sur-Seine (FR)

(73) Assignees: LES LABORATOIRES SERVIER, Suresnes (FR); NOVARTIS AG, Basel (CH)

( * ) Notice: Subject to any disclaimer, the term of this patent is extended or adjusted under 35 U.S.C. 154(b) by 0 days.

(21) Appl. No.: 16/622,967

(22) PCT Filed: Jun. 21, 2018

(86) PCT No.: PCT/EP2018/066551
§ 371 (c)(1),
(2) Date: Dec. 16, 2019

(87) PCT Pub. No.: WO2018/234433
PCT Pub. Date: Dec. 27, 2018

(65) Prior Publication Data
US 2020/0392151 A1   Dec. 17, 2020

Related U.S. Application Data

(60) Provisional application No. 62/523,389, filed on Jun. 22, 2017.

(30) Foreign Application Priority Data

Sep. 6, 2017 (EP) ................................ 17189550

(51) Int. Cl.
| | |
|---|---|
| C07D 495/04 | (2006.01) |
| A61P 35/02 | (2006.01) |
| A61K 9/00 | (2006.01) |
| A61K 31/704 | (2006.01) |
| A61K 31/7068 | (2006.01) |

(52) U.S. Cl.
CPC ............ *C07D 495/04* (2013.01); *A61P 35/02* (2018.01); *A61K 9/0053* (2013.01); *A61K 31/704* (2013.01); *A61K 31/7068* (2013.01)

(58) Field of Classification Search
None
See application file for complete search history.

(56) References Cited

U.S. PATENT DOCUMENTS

2019/0062428 A1* 2/2019 Paterson ............ C07K 16/2803

OTHER PUBLICATIONS

Partial Substance Detail entry for CAS Registry No. 1799633-27-4 downlaoded from https://scifinder.cas.org/scifinder/view/scidiner/scifinderExplore.jsf on Aug. 3, 2021.*
Partial Substance Detail entry for CAS Registry No. 1799631-75-6 downloaded from https://scifiner.cas.org/scifinder/view/scifinder/scifinderExplore.jsf on Aug. 3, 2021.*
International Search Report for PCT/EP2018/066551 dated 22 Aug. 2018.
Letai, Anthony, "S63845, an MCL-1 selective BH3 mimetic: another arrow in our quiver", Cancer Cell, 30, Dec. 12, 2016, pp. 834-835.
Levy, Michelle, A., et al., "Therapeutic inhibition of BCL-2 and related family members", Expert Opinion on Investigational Drugs, 26:3, 2017, pp. 293-301.
Lehar et al., Nature Biotechnology 2009, 27(7), 659-66.

* cited by examiner

*Primary Examiner* — Brian J Davis
(74) *Attorney, Agent, or Firm* — Hueschen and Sage

(57) ABSTRACT

A combination comprising a Mcl-1 inhibitor and a second anticancer agent, wherein the second anticancer agent is selected from anthracyclines, cytarabine and hypomethylating agents, and compositions and uses thereof.

25 Claims, 6 Drawing Sheets

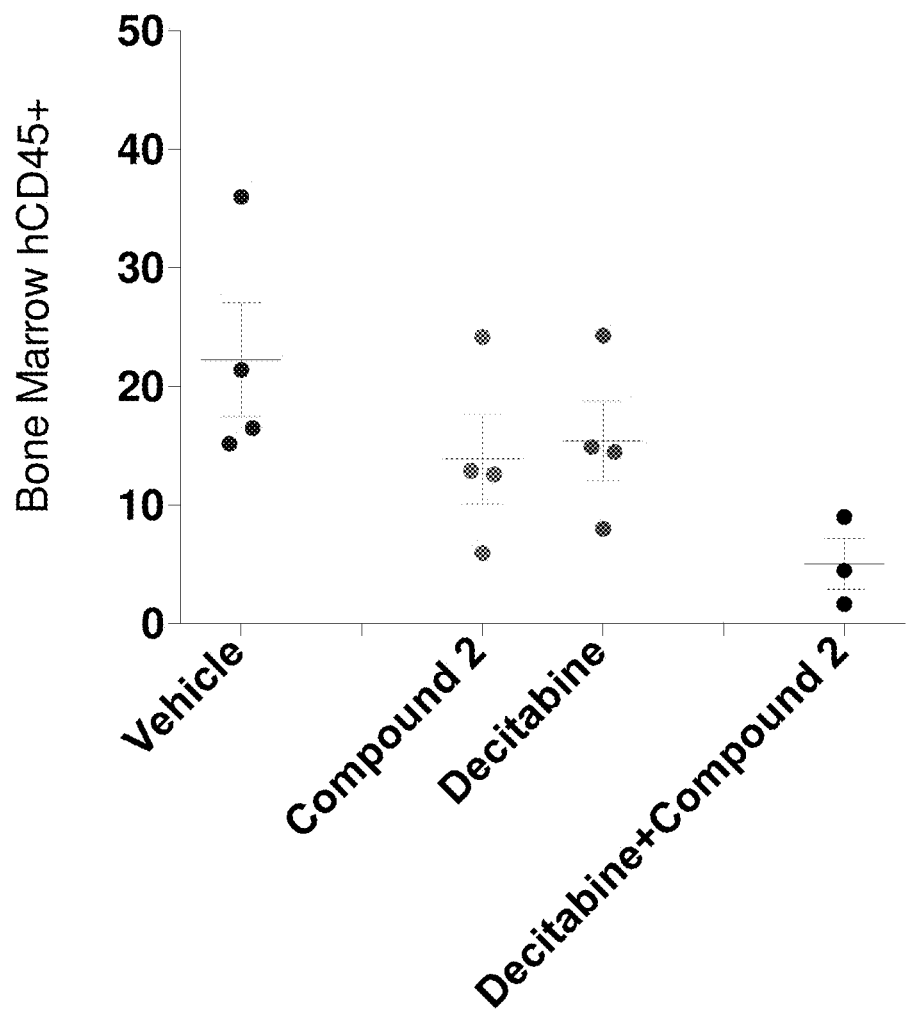

COMBINATION OF A MCL-1 INHIBITOR AND A STANDARD OF CARE TREATMENT FOR HEMATOLOGIC CANCERS, USES AND PHARMACEUTICAL COMPOSITIONS THEREOF

FIELD OF THE INVENTION

The present invention relates to a combination of a Mcl-1 inhibitor with a second anticancer agent, wherein the second anticancer agent is selected from anthracyclines (such as idarubicin, daunorubicin . . . ), cytarabine (also known as cytosine arabinoside or ara-C) and hypomethylating agents (such as decitabine, azacitidine . . . ). The present invention relates to a combination of a Mcl-1 inhibitor with a second anticancer agent, wherein the second anticancer agent is selected from idarubicin, daunorubicin, mitoxantrone, cytarabine, decitabine, azacitidine and guadecitabine, more particularly idarubicin, daunorubicin, cytarabine, decitabine and azacitidine. The invention also relates to the use of said combination in the treatment of cancer, in particular hematologic cancer, and more particularly acute myeloid leukemia (AML), myelodysplastic syndromes, acute lymphocytic leukemia (ALL) and lymphoma. Also provided are pharmaceutical formulations suitable for the administration of such combinations.

The presence of multiple acquired mutations within multiple clones in each AML case makes the concept of successful selective targeting particularly difficult. This invention proposes the concept that cancers with diverse and multi-clonal molecular compositions may be successfully treated with the combination of an inhibitor of Mcl-1 and a cytotoxic drug able to effectively activate cellular apoptosis in a promiscuous manner, thereby leading to broad-based cell death of cancer cells beyond that achieved using Mcl-1 inhibitors or standard-of-care (SOC) chemotherapy separately. This approach could lead to enhanced rates of remission and increased clearance of minimal residual disease in the induction chemotherapy setting and this may lead to reduced rates of disease relapse and higher overall cure rates in AML as an example. AML is proposed as a model example due to the ability to quantitatively measure changes in clonal composition serially with treatment using digital PCR and RT-qPCR.

Inhibitors of Mcl-1 when combined with low-dose SOC chemotherapy could enhance the targeting of leukemic stem and progenitor cells by lowering the apoptotic threshold. This approach could be used in the post-remission setting as a maintenance therapy approach to eliminate residual AML stem cells and pre-leukemic stem cell clones comprised of diverse molecular and cytogenetic abnormalities. The principle of demonstrating the eradication of leukemic and pre-leukemic progenitors will be demonstrated by reducing levels of clonal minimal residual disease or pre-leukemic clones as measured in differentiated mononuclear cells in the post-remission setting after exposure to Mcl-1 inhibitors in combination with SOC chemotherapy.

BACKGROUND OF THE INVENTION

Apoptosis is a highly regulated cell death pathway that is initiated by various cytotoxic stimuli, including oncogenic stress and chemotherapeutic agents. It has been shown that evasion of apoptosis is a hallmark of cancer and that efficacy of many chemotherapeutic agents is dependent upon the activation of the intrinsic mitochondrial pathway. Three distinct subgroups of the Bcl-2 family proteins control the intrinsic apoptosis pathway: (i) the pro-apoptotic BH3 (the Bcl-2 homology 3)-only proteins; (ii) the pro-survival members such as Bcl-2 itself, Bcl-xl, Bcl-w, Mcl-1 and Bcl-2a1; and (iii) the pro-apoptotic effector proteins BAX and BAK (Czabotar et al., *Nature Reviews Molecular Cell Biology* 2014, 15, 49-63). Overexpression of the anti-apoptotic members of Bcl-2 family is observed in many cancers, particularly in hematological malignancies such as mantle cell lymphoma (MCL), follicular lymphoma/diffuse large B-cell lymphoma (FL/DLCL) and multiple myeloma (Adams and Cory, *Oncogene* 2007, 26, 1324-1337). Pharmacological inhibition of the anti-apoptotic proteins Bcl-2, Bcl-xl, Bcl-w and Mcl-1 by the recently developed BH3-mimetics drugs such as ABT-199 (venetoclax), ABT-263 (navitoclax) and S63845 has emerged as a therapeutic strategy to induce apoptosis and cause tumor regression in cancer (Zhang et al., *Drug Resist. Updat.* 2007, 10, 207-217; Kotschy et al., *Nature* 2016, 538, 477-482). Nevertheless, mechanisms of resistance to BH3 mimetics have been observed (Choudhary et al., *Cell Death and Disease* 2015, 6, e1593) and the use of combination therapies could improve efficacy and delay or even abrogate resistance development.

Acute myeloid leukemia (AML) is a rapidly fatal blood cancer arising from clonal transformation of hematopoietic stem cells resulting in paralysis of normal bone marrow function and deaths due to complications from profound pancytopenia. AML accounts for 25% of all adult leukemias, with the highest incidence rates occurring in the United States, Australia and Europe (WHO. GLOBOCAN 2012. Estimated cancer incidence, mortality and prevalence worldwide in 2012. International Agency for Research on Cancer). Globally, there are approximately 88,000 new cases diagnosed annually. AML continues to have the lowest survival rate of all leukemias, with expected 5-year survival of only 24%.

Current therapies for the treatment of AML include the administration of cytarabine alone or in combination with an anthracycline such as daunorubicin or idarubicin. Low-dose cytarabine treatment and demethylating agents such as azacitidine and decitabine are also recommended as low-intensity options for patients who are ineligible for intensive chemotherapy (Döhner et al., DOI 10.1182/blood-2016-08-733196). Although the standard therapy for AML (cytarabine in combination with anthracyclines) was conceived over 4 decades ago, the introduction of successful targeted therapies for this disease has remained an elusive goal. The concept of targeted therapy in AML has been hampered by the realization that this disease evolves as a multi-clonal hierarchy, with rapid outgrowth of leukemic sub-clones as a major cause of drug resistance and disease relapse (Ding et al., *Nature* 2012, 481, 506-510). Recent clinical investigations have demonstrated the efficacy of Bcl-2 inhibitors in the treatment of AML (Konopleva et al., *American Society of Hematology* 2014, 118).

There remains a need for new treatments and therapies for the treatment of hematologic cancer, in particular AML, myelodysplastic syndromes, ALL and lymphoma, and more particularly for the treatment of AML. The present invention provides a novel combination of a Mcl-1 inhibitor and a second anticancer agent, wherein the second anticancer agent is selected from anthracyclines, cytarabine and hypomethylating agents, more particularly idarubicin, daunorubicin, mitoxantrone, cytarabine, decitabine, azacitidine and guadecitabine, and more preferably idarubicin, daunorubicin, cytarabine, decitabine and azacitidine. The results show that the Mcl-1 inhibitor in combination with a second anticancer agent, wherein the second anticancer agent is selected from idarubicin, cytarabine and decitabine interacts synergistically in AML cell lines (FIG. 1; Tables 3, 4 and 5). We also show that the combination of a Mcl-1 inhibitor with a second anticancer agent, wherein the second anticancer agent is selected from idarubicin or decitabine exhibits a synergistic pro-apoptotic activity in primary human AML samples (FIGS. 2 and 6; Table 6). We also show that a subset of primary AML samples were sensitive to the combination of a Mcl-1 inhibitor with cytarabine whereas normal human CD34+ progenitor cells were resistant to the same dose (FIG. 3). We also show that Mcl-1 inhibitor combined with decitabine was well-tolerated without losing weight during treatment and yet leads to enhanced activity against human AML in a patient-derived xenograft model in vivo (FIGS. 4, 5 and 6). Finally, we show that the combination of a Mcl-1 inhibitor with cytarabine could provide benefit to the treatment of ALL patients (Table 7).

SUMMARY OF THE INVENTION

The present invention relates to a combination comprising:
(a) a Mcl-1 inhibitor of formula (I):

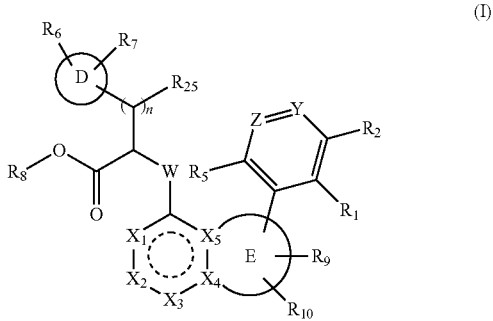

wherein:
D represents a cycloalkyl group, a heterocycloalkyl group, an aryl group or a heteroaryl group,
E represents a furyl, thienyl or pyrrolyl ring,
$X_1$, $X_3$, $X_4$ and $X_5$ independently of one another represent a carbon atom or a nitrogen atom,
$X_2$ represents a C—$R_{26}$ group or a nitrogen atom, ◯ means that the ring is aromatic,
Y represents a nitrogen atom or a C—$R_3$ group,
Z represents a nitrogen atom or a C—$R_4$ group,
$R_1$ represents a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl group, a hydroxy group, a hydroxy($C_1$-$C_6$)alkyl group, a linear or branched ($C_1$-$C_6$)alkoxy group, —S—($C_1$-$C_6$)alkyl group, a cyano group, a nitro group, -$Cy_8$, -alkyl($C_0$-$C_6$)—$NR_{11}R_{11}'$, —O-alkyl($C_1$-$C_6$)—$NR_{11}R_{11}'$, —O-alkyl($C_1$-$C_6$)—$R_{12}$, —C(O)—$OR_{11}$, —O—C (O)—$R_{11}$, —C(O)—$NR_{11}R_{11}'$, —$NR_{11}$—C(O)—$R_{11}'$, —$NR_{11}$—C(O)—$OR_{11}'$, -alkyl($C_1$-$C_6$)—$NR_{11}$—C (O)—$R_{11}'$, —$SO_2$—$NR_{11}R_{11}'$, or —$SO_2$-alkyl($C_1$-$C_6$),
$R_2$, $R_3$, $R_4$ and $R_5$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a hydroxy($C_1$-$C_6$)alkyl group, a linear or branched ($C_1$-$C_6$)alkoxy group, a —S—($C_1$-$C_6$)alkyl group, a cyano group, a nitro group, -alkyl($C_0$-$C_6$)—$NR_{11}R_{11}'$, —O-$Cy_1$, -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$NR_{11}R_{11}'$, —O-alkyl($C_1$-$C_6$)—$R_{12}$, —C(O)—$OR_{11}$, —O—C(O)—$R_{11}$, —C(O)—$NR_{11}R_{11}'$, —$NR_{11}$—C (O)—$R_{11}'$, —$NR_{11}$—C(O)—$OR_{11}'$, -alkyl($C_1$-$C_6$)—$NR_{11}$—C(O)—$R_{11}'$, —$SO_2$—$NR_{11}R_{11}'$, or —$SO_2$-alkyl($C_1$-$C_6$),
or the substituents of the pair ($R_1$, $R_2$), ($R_2$, $R_3$), ($R_3$, $R_4$), ($R_4$, $R_5$) form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by from 1 to 2 groups selected from halogen, linear or branched ($C_1$-$C_6$)alkyl, -alkyl($C_0$-$C_6$)—$NR_{11}R_{11}'$, —$NR_{13}R_{13}'$, -alkyl($C_0$-$C_6$)-$Cy_1$ or oxo,
$R_6$ and $R_7$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a linear or branched ($C_1$-$C_6$)alkoxy group, a —S—($C_1$-$C_6$)alkyl group, a cyano group, a nitro group, -alkyl($C_0$-$C_6$)—$NR_{11}R_{11}'$, —O-alkyl($C_1$-$C_6$)—$NR_{11}R_{11}'$, —O-$Cy_1$, -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl($C_1$-$C_6$)—$NR_{11}$—C(O)—$R_{11}'$, —$SO_2$—$NR_{11}R_{11}'$, or —$SO_2$-alkyl($C_1$-$C_6$),
or the substituents of the pair ($R_6$, $R_7$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched ($C_1$-$C_6$)alkyl group, —$NR_{13}R_{13}'$, -alkyl($C_0$-$C_6$)-$Cy_1$ or an oxo,
W represents a —$CH_2$— group, a —NH— group or an oxygen atom,
$R_8$ represents a hydrogen atom, a linear or branched ($C_1$-$C_8$)alkyl group, a —$CHR_aR_b$ group, an aryl group, a heteroaryl group, an arylalkyl($C_1$-$C_6$) group, or a heteroarylalkyl($C_1$-$C_6$) group,
$R_9$ represents a hydrogen atom, a linear or branched ($C_1$-$C_6$)alkyl group, a linear or branched ($C_2$-$C_6$)alkenyl group, a linear or branched ($C_2$-$C_6$)alkynyl group, -$Cy_2$, -alkyl($C_1$-$C_6$)-$Cy_2$, -alkenyl($C_2$-$C_6$)-$Cy_2$, -alkynyl($C_2$-$C_6$)-$Cy_2$, -$Cy_2$-$Cy_3$, -alkynyl($C_2$-$C_6$)—O-$Cy_2$, -$Cy_2$-alkyl($C_0$-$C_6$)—O-alkyl($C_0$-$C_6$)-$Cy_3$, a halogen atom, a cyano group, —C(O)—$R_{14}$, or —C(O)—$NR_{14}R_{14}'$,
$R_{10}$ represents a hydrogen atom, a linear or branched ($C_1$-$C_6$)alkyl group, a linear or branched ($C_2$-$C_6$)alkenyl group, a linear or branched ($C_2$-$C_6$)alkynyl group, an arylalkyl($C_1$-$C_6$) group, a cycloalkylalkyl($C_1$-$C_6$) group, a linear or branched ($C_1$-$C_6$)polyhaloalkyl, or -alkyl($C_1$-$C_6$)—O-$Cy_4$,
or the substituents of the pair ($R_9$, $R_{10}$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, $R_{11}$ and $R_{11}'$ independently of one another represent a hydrogen atom, an optionally substituted linear or branched $(C_1-C_6)$alkyl group, or -alkyl$(C_1-C_6)$-$Cy_1$, or the substituents of the pair $(R_{11}, R_{11}')$ form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the nitrogen in question may be substituted by from 1 to 2 groups representing a hydrogen atom, or a linear or branched $(C_1-C_6)$alkyl group and it being understood that one or more of the carbon atoms of the possible substituents, may be deuterated, $R_{12}$ represents -$Cy_5$, -$Cy_5$-alkyl$(C_1-C_6)$—O-alkyl$(C_1-C_6)$-$Cy_6$, -$Cy_5$-alkyl$(C_1-C_6)$-$Cy_6$, -$Cy_5$-alkyl$(C_0-C_6)$—$NR_{11}$-alkyl$(C_0-C_6)$-$Cy_6$, -$Cy_5$-$Cy_6$-O-alkyl$(C_0-C_6)$-$Cy_7$, -$Cy_5$-alkyl$(C_0-C_6)$—O-alkyl$(C_0-C_6)$-$Cy_9$, -$Cy_5$-alkyl$(C_0-C_6)$-$Cy_9$, —NH—C(O)—NH—$R_{11}$, -$Cy_5$-alkyl$(C_0-C_6)$—$NR_{11}$-alkyl$(C_0-C_6)$-$Cy_9$, —C(O)—$NR_{11}R_{11}'$, —$NR_{11}R_{11}'$, —OR, —$NR_{11}$—C(O)—$R_{11}'$, —O-alkyl$(C_1-C_6)$—$OR_{11}$, —$SO_2$—$R_{11}$, —C(O)—OR,

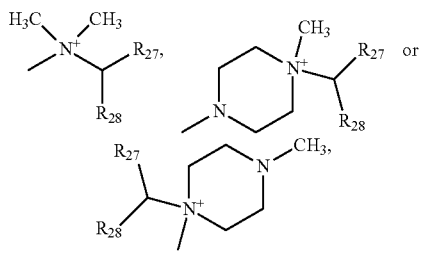

it being possible for the ammonium so defined to exist as a zwitterionic form or to have a monovalent anionic counterion, $R_{13}$, $R_{13}'$, $R_{14}$ and $R_{14}'$ independently of one another represent a hydrogen atom, or an optionally substituted linear or branched $(C_1-C_6)$alkyl group, $R_a$ represents a hydrogen atom or a linear or branched $(C_1-C_6)$alkyl group, $R_b$ represents a —O—C(O)—O—$R_c$ group, a —O—C(O)—$NR_cR_c'$ group, or a —O—P(O)$(OR_c)_2$ group, $R_c$ and $R_c'$ independently of one another represent a hydrogen atom, a linear or branched $(C_1-C_8)$alkyl group, a cycloalkyl group, a $(C_1-C_6)$alkoxy$(C_1-C_6)$alkyl group, or a $(C_1-C_6)$alkoxycarbonyl$(C_1-C_6)$alkyl group, or the substituents of the pair $(R_c, R_c')$ form together with the nitrogen atom carrying them a non-aromatic ring composed of from 5 to 7 ring members, which may contain in addition to the nitrogen atom from 1 to 3 heteroatoms selected from oxygen and nitrogen, it being understood that the nitrogen in question may be substituted by a group representing a linear or branched $(C_1-C_6)$alkyl group, $Cy_1$, $Cy_2$, $Cy_3$, $Cy_4$, $Cy_5$, $Cy_6$, $Cy_7$, $Cy_8$ and $Cy_{10}$ independently of one another, represent a cycloalkyl group, a heterocycloalkyl group, an aryl group or a heteroaryl group, $Cy_9$ represents

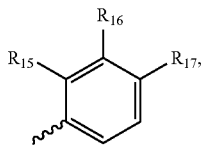

or $Cy_9$ represents a heteroaryl group which is substituted by a group selected from —O—P(O)$(OR_{20})_2$; —O—P(O)$(O^-M^+)_2$; —$(CH_2)_p$—O—$(CHR_{18}$—$CHR_{19}$—O$)_q$—$R_{20}$; hydroxy; hydroxy$(C_1-C_6)$alkyl; —$(CH_2)_r$—U—$(CH_2)_s$-heterocycloalkyl; or —U—$(CH_2)_q$—$NR_{21}R_{21}'$, $R_{15}$ represents a hydrogen atom; a —$(CH_2)_p$—O—$(CHR_{18}$—$CHR_{19}$—O$)_q$—$R_{20}$ group; a linear or branched $(C_1-C_6)$alkoxy$(C_1-C_6)$alkyl group; a —U—$(CH_2)_q$—$NR_{21}R_{21}'$ group; or a —$(CH_2)_r$—U—$(CH_2)_s$-heterocycloalkyl group, $R_{16}$ represents a hydrogen atom; a hydroxy group; a hydroxy$(C_1-C_6)$alkyl group; a —$(CH_2)_r$—U—$(CH_2)_s$-heterocycloalkyl group; a $(CH_2)_r$—U—V—O—P(O)$(OR_{20})_2$ group; a —O—P(O)$(O^-M^+)_2$ group; a —$(CH_2)_p$—O—$(CHR_{18}$—$CHR_{19}$—O$)_q$—$R_{20}$ group; a —$(CH_2)_p$—O—C(O)—$NR_{22}R_{23}$ group; or a —U—$(CH_2)_q$—$NR_{21}R_{21}'$ group, $R_{17}$ represents a hydrogen atom; a —$(CH_2)_p$—O—$(CHR_{18}$—$CHR_{19}$—O$)_q$—$R_{20}$ group; a —O—P(O)$(OR_{20})_2$ group; a —O—P(O)$(O^-M^+)_2$ group; a hydroxy group; a hydroxy$(C_1-C_6)$alkyl group; a —$(CH_2)_r$—U—$(CH_2)_s$-heterocycloalkyl group; a —U—$(CH_2)_q$—$NR_{21}R_{21}'$ group; or an aldonic acid, $M^+$ represents a pharmaceutically acceptable monovalent cation, U represents a bond or an oxygen atom, V represents a —$(CH_2)_s$— group or a —C(O)— group, $R_{18}$ represents a hydrogen atom or a $(C_1-C_6)$alkoxy$(C_1-C_6)$alkyl group, $R_{19}$ represents a hydrogen atom or a hydroxy$(C_1-C_6)$alkyl group, $R_{20}$ represents a hydrogen atom or a linear or branched $(C_1-C_6)$alkyl group, $R_{21}$ and $R_{21}'$ independently of one another represent a hydrogen atom, a linear or branched $(C_1-C_6)$alkyl group, or a hydroxy$(C_1-C_6)$alkyl group, or the substituents of the pair $(R_{21}, R_{21}')$ form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the resulting ring may be substituted by a group representing a hydrogen atom or a linear or branched $(C_1-C_6)$ alkyl group, $R_{22}$ represents a $(C_1-C_6)$alkoxy$(C_1-C_6)$alkyl group, a —$(CH_2)_p$—$NR_{24}R_{24}'$ group, or a —$(CH_2)_p$—O—$(CHR_{18}$—$CHR_{19}$—O$)_q$—$R_{20}$ group, $R_{23}$ represents a hydrogen atom or a $(C_1-C_6)$alkoxy$(C_1-C_6)$alkyl group, or the substituents of the pair $(R_{22}, R_{23})$ form together with the nitrogen atom carrying them an aromatic or non-aromatic ring composed of from 5 to 18 ring members, which may contain in addition to the nitrogen atom from 1 to 5 heteroatoms selected from oxygen, sulphur and nitrogen, it being understood that the resulting ring may be substituted by a group representing a hydrogen atom, a linear or branched $(C_1-C_6)$alkyl group or a heterocycloalkyl group, R$_{24}$ and R$_{24}$' independently of one another represent a hydrogen atom or a linear or branched (C$_1$-C$_6$)alkyl group, or the substituents of the pair (R$_{24}$, R$_{24}$') form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the resulting ring may be substituted by a group representing a hydrogen atom or a linear or branched (C$_1$-C$_6$) alkyl group, R$_{25}$ represents a hydrogen atom, a hydroxy group, or a hydroxy(C$_1$-C$_6$)alkyl group, R$_{26}$ represents a hydrogen atom, a halogen atom, a linear or branched (C$_1$-C$_6$)alkyl group, or a cyano group, R$_{27}$ represents a hydrogen atom or a linear or branched (C$_1$-C$_6$)alkyl group, R$_{28}$ represents a —O—P(O)(O$^-$)(O$^-$) group, a —O—P(O)(O$^-$)(OR$_{30}$) group, a —O—P(O)(OR$_{30}$)(OR$_{30}$') group, a —O—SO$_2$—O$^-$ group, a —O—SO$_2$—OR$_{30}$ group, -Cy$_{10}$, a —O—C(O)—R$_{29}$ group, a —O—C(O)—OR$_{29}$ group or a —O—C(O)—NR$_{29}$R$_{29}$' group;

R$_{29}$ and R$_{29}$' independently of one another represent a hydrogen atom, a linear or branched (C$_1$-C$_6$)alkyl group or a linear or branched amino(C$_1$-C$_6$)alkyl group, R$_{30}$ and R$_{30}$' independently of one another represent a hydrogen atom, a linear or branched (C$_1$-C$_6$)alkyl group or an arylalkyl(C$_1$-C$_6$) group, n is an integer equal to 0 or 1, p is an integer equal to 0, 1 or 2, q is an integer equal to 1, 2, 3 or 4, r and s are independently an integer equal to 0 or 1, it being understood that:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, it being possible for the aryl, heteroaryl, cycloalkyl and heterocycloalkyl groups so defined and the alkyl, alkenyl, alkynyl, alkoxy, to be substituted by from 1 to 4 groups selected from optionally substituted linear or branched (C$_1$-C$_6$)alkyl, optionally substituted linear or branched (C$_2$-C$_6$) alkenyl group, optionally substituted linear or branched (C$_2$-C$_6$)alkynyl group, optionally substituted linear or branched (C$_1$-C$_6$)alkoxy, optionally substituted (C$_1$-C$_6$)alkyl-S—, hydroxy, oxo (or N-oxide where appropriate), nitro, cyano, —C(O)—OR', —O—C(O)—R', —C(O)—NR"R", —NR'R", —(C=NR')—OR", linear or branched (C$_1$-C$_6$) polyhaloalkyl, trifluoromethoxy, or halogen, it being understood that R' and R" independently of one another represent a hydrogen atom or an optionally substituted linear or branched (C$_1$-C$_6$)alkyl group, and it being understood that one or more of the carbon atoms of the preceding possible substituents, may be deuterated, or their enantiomers, diastereoisomers, atropisomers, or addition salts thereof with a pharmaceutically acceptable acid or base, and (b) a second anticancer agent, wherein the second anticancer agent is selected from anthracyclines, cytarabine and hypomethylating agents, for simultaneous, sequential or separate use.

Said compounds of formula (I), their synthesis, their use in the treatment of cancer and pharmaceutical formulations thereof, are described in WO 2015/097123, WO 2016/207216, WO 2016/207217, WO 2016/207225, WO 2016/207226, and WO 2017/125224, the contents of which are incorporated by reference.

According to a first aspect of the invention, there is provided a combination comprising:

(a) a Mcl-1 inhibitor of formula (II), a particular case of Mcl-1 inhibitor of formula (I):

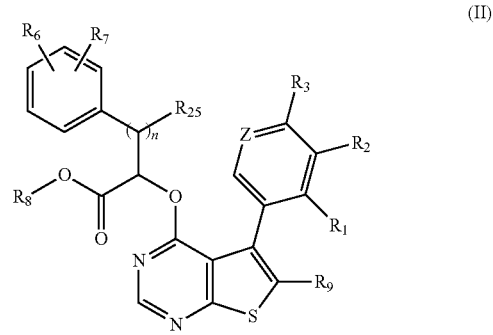

(II)

wherein:

Z represents a nitrogen atom or a C—R$_4$ group,

R$_1$ represents a linear or branched (C$_1$-C$_6$)alkyl group, a linear or branched (C$_2$-C$_6$)alkenyl group, a linear or branched (C$_2$-C$_6$)alkynyl group, a linear or branched (C$_1$-C$_6$)alkoxy group, —S—(C$_1$-C$_6$)alkyl group, a linear or branched (C$_1$-C$_6$)polyhaloalkyl, a hydroxy group, a cyano, —NR$_{11}$R$_{11}$', -Cy$_8$ or a halogen atom, R$_2$, R$_3$ and R$_4$ independently of one another represent a hydrogen atom, a halogen atom, a linear or branched (C$_1$-C$_6$)alkyl group, a linear or branched (C$_2$-C$_6$)alkenyl group, a linear or branched (C$_2$-C$_6$)alkynyl group, a linear or branched (C$_1$-C$_6$)polyhaloalkyl, a hydroxy group, a linear or branched (C$_1$-C$_6$)alkoxy group, —S—(C$_1$-C$_6$)alkyl group, a cyano group, a nitro group, -alkyl(C$_0$-C$_6$)—NR$_{11}$R$_{11}$', —O-Cy$_1$, -alkyl(C$_0$-C$_6$)-Cy$_1$, -alkenyl(C$_2$-C$_6$)-Cy$_1$, -alkynyl(C$_2$-C$_6$)-Cy$_1$, —O-alkyl(C$_1$-C$_6$)—R$_{12}$, —C(O)—OR$_{11}$, —O—C(O)—R$_{11}$, —C(O)—NR$_{11}$R$_{11}$', —NR$_{11}$—C(O)—R$_{11}$', —NR$_{11}$—C(O)—OR$_{11}$', -alkyl(C$_1$-C$_6$)—NR$_{11}$—C(O)—R$_{11}$', —SO$_2$—NR$_{11}$R$_{11}$', or —SO$_2$-alkyl(C$_1$-C$_6$), or the substituents of one of the pairs (R$_2$, R$_3$), (R$_3$, R$_4$) form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched (C$_1$-C$_6$)alkyl group, —NR$_{13}$R$_{13}$', -alkyl(C$_0$-C$_6$)-Cy$_1$ or an oxo, R$_6$ and R$_7$ independently of one another represent a hydrogen atom, a halogen atom, a linear or branched (C$_1$-C$_6$)alkyl group, a linear or branched (C$_2$-C$_6$)alkenyl group, a linear or branched (C$_2$-C$_6$)alkynyl group, a linear or branched ($C_1$-$C_6$)polyhaloalkyl, a hydroxy group, a linear or branched ($C_1$-$C_6$)alkoxy group, a —S—($C_1$-$C_6$)alkyl group, a cyano group, a nitro group, -alkyl($C_0$-$C_6$)—$NR_{11}R_{11}$', —O-$Cy_1$, -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$R_{12}$, —C(O)—$OR_{11}$, —O—C(O)—$R_{11}$, —C(O)—$NR_{11}R_{11}$', —$NR_{11}$—C(O)—$R_{11}$', —$NR_{11}$—C(O)—$OR_{11}$', -alkyl($C_1$-$C_6$)—$NR_{11}$—C(O)—$R_{11}$', —$SO_2$—$NR_{11}R_{11}$', or —$SO_2$-alkyl($C_1$-$C_6$), or the substituents of the pair ($R_6$, $R_7$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched ($C_1$-$C_6$)alkyl group, —$NR_{13}R_{13}$', -alkyl($C_0$-$C_6$)-$Cy_1$ or an oxo, $R_8$ represents a hydrogen atom, a linear or branched ($C_1$-$C_8$)alkyl group, an aryl group, a heteroaryl group, an arylalkyl($C_1$-$C_6$) group, or a heteroarylalkyl($C_1$-$C_6$) group, $R_9$ represents a linear or branched ($C_1$-$C_6$)alkyl group, a linear or branched ($C_2$-$C_6$)alkenyl group, a linear or branched ($C_2$-$C_6$)alkynyl group, -$Cy_2$, -alkyl($C_1$-$C_6$)-$Cy_2$, -alkenyl($C_2$-$C_6$)-$Cy_2$, -alkynyl($C_2$-$C_6$)-$Cy_2$, -$Cy_2$-$Cy_3$, -alkynyl($C_2$-$C_6$)—O-$Cy_2$, -$Cy_2$-alkyl($C_0$-$C_6$)—O-alkyl($C_0$-$C_6$)-$Cy_3$, a halogen atom, a cyano group, —C(O)—$R_{14}$, or —C(O)—$NR_{14}R_{14'}$, $R_{11}$ and $R_{11}$' independently of one another represent a hydrogen atom, an optionally substituted linear or branched ($C_1$-$C_6$)alkyl group, or -alkyl($C_0$-$C_6$)-$Cy_1$, or the substituents of the pair ($R_{11}$, $R_{11}$') form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the nitrogen in question may be substituted by a group representing a hydrogen atom, or a linear or branched ($C_1$-$C_6$)alkyl group and it being understood that one or more of the carbon atoms of the possible substituents, may be deuterated, $R_{12}$ represents -$Cy_5$, -$Cy_5$-alkyl($C_0$-$C_6$)-$Cy_6$, -$Cy_5$-alkyl ($C_0$-$C_6$)—O-alkyl($C_0$-$C_6$)-$Cy_6$, -$Cy_5$-alkyl($C_0$-$C_6$)—$NR_{11}$-alkyl($C_0$-$C_6$)-$Cy_6$, -$Cy_5$-$Cy_6$-O-alkyl($C_0$-$C_6$)-$Cy_7$, —C(O)—$NR_{11}R_{11}$', —$NR_{11}R_{11}$', —$OR_{11}$, —$NR_{11}$—C(O)—$R_{11}$', —O-alkyl($C_1$-$C_6$)—$OR_{11}$, —$SO_2$—$R_1$, —C(O)—$OR_{11}$, or —NH—C(O)—NH—$R_{II}$, $R_{13}$, $R_{13}$', $R_{14}$ and $R_{14}$' independently of one another represent a hydrogen atom, or an optionally substituted linear or branched ($C_1$-$C_6$)alkyl group, $R_{25}$ represents a hydrogen atom, a hydroxy group, or a hydroxy($C_1$-$C_6$)alkyl group, $Cy_1$, $Cy_2$, $Cy_3$, $Cy_5$, $Cy_6$, $Cy_7$ and $Cy_8$ independently of one another, represent a cycloalkyl group, a heterocycloalkyl group, an aryl group or a heteroaryl group, n is an integer equal to 0 or 1, it being understood that:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, it being possible for the aryl, heteroaryl, cycloalkyl and heterocycloalkyl groups so defined and the alkyl, alkenyl, alkynyl, alkoxy, to be substituted by from 1 to 4 groups selected from optionally substituted linear or branched ($C_1$-$C_6$)alkyl, optionally substituted linear or branched ($C_2$-$C_6$) alkenyl group, optionally substituted linear or branched ($C_2$-$C_6$)alkynyl group, optionally substituted linear or branched ($C_1$-$C_6$)alkoxy, optionally substituted ($C_1$-$C_6$)alkyl-S—, hydroxy, oxo (or N-oxide where appropriate), nitro, cyano, —C(O)—OR', —O—C(O)—R', —C(O)—NR'R", —NR'R", —(C=NR')—OR", linear or branched ($C_1$-$C_6$) polyhaloalkyl, trifluoromethoxy, or halogen, it being understood that R' and R" independently of one another represent a hydrogen atom or an optionally substituted linear or branched ($C_1$-$C_6$)alkyl group, and it being understood that one or more of the carbon atoms of the preceding possible substituents, may be deuterated, or their enantiomers, diastereoisomers, atropisomers, or addition salts thereof with a pharmaceutically acceptable acid or base, and (b) a second anticancer agent, wherein the second anticancer agent is selected from anthracyclines, cytarabine and hypomethylating agents, for simultaneous, sequential or separate use.

In a first embodiment, the invention provides a combination comprising:

(a) Compound 1: (2R)-2-{[(5S$_a$)-5-{3-chloro-2-methyl-4-[2-(4-methylpiperazin-1-yl) ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, or a pharmaceutically acceptable salt thereof, and (b) a second anticancer agent, wherein the second anticancer agent is selected from anthracyclines, cytarabine and hypomethylating agents, for simultaneous, sequential or separate use.

Alternatively, the invention provides a combination comprising:

(a) Compound 2: (2R)-2-{[(5S$_a$)-5-{3-chloro-2-methyl-4-[2-(4-methylpiperazin-1-yl) ethoxy]phenyl}-6-(5-fluorofuran-2-yl)thieno[2,3-d]pyrimidin-4-yl]oxy}-3-(2-{[1-(2,2,2-trifluoroethyl)-1H-pyrazol-5-yl]methoxy}phenyl) propanoic acid, or a pharmaceutically acceptable salt thereof, and (b) a second anticancer agent, wherein the second anticancer agent is selected from anthracyclines, cytarabine and hypomethylating agents, for simultaneous, sequential or separate use.

In a particular embodiment, the second anticancer agent is an anthracycline selected from idarubicin, daunorubicin and mitoxantrone, more particularly, idarubicin and daunorubicin, even more particularly, idarubicin.

In a particular embodiment, the second anticancer agent is a hypomethylating agent selected from decitabine, azacitidine and guadecitabine, more particularly, decitabine and azacitidine, even more particularly, decitabine.

In a particular embodiment, the second anticancer agent is idarubicin, daunorubicin, cytarabine, decitabine and azacitidine, more preferably, idarubicin, cytarabine and decitabine.

In another embodiment, the invention provides a combination as described herein, for use in the treatment of cancer, more particularly, the treatment of hematologic cancer. The treatment of AML, myelodysplastic syndromes, acute lymphocytic leukemia and lymphoma is particularly preferred. More particularly, the treatment of AML is preferred.

In another embodiment, the invention provides the use of a combination as described herein, in the manufacture of a medicament for the treatment of cancer, more particularly, the treatment of hematologic cancer, even more particularly the treatment of AML, myelodysplastic syndromes, acute lymphocytic leukemia and lymphoma.

In another embodiment, the invention provides a medicament containing, separately or together,
(a) a Mcl-1 inhibitor of formula (I) and
(b) a second anticancer agent, wherein the second anticancer agent is selected from anthracyclines, cytarabine and hypomethylating agents,
or
(a) a Mcl-1 inhibitor of formula (II) as described herein, and
(b) a second anticancer agent, wherein the second anticancer agent is selected from anthracyclines, cytarabine and hypomethylating agents,
for simultaneous, sequential or separate administration, and wherein the Mcl-1 inhibitor and the second anticancer agent are provided in effective amounts for the treatment of cancer.

In another embodiment, the invention provides a method of treating cancer, comprising administering a jointly therapeutically effective amount of:
(a) a Mcl-1 inhibitor of formula (I) and
(b) a second anticancer agent, wherein the second anticancer agent is selected from anthracyclines, cytarabine and hypomethylating agents,
or
(a) a Mcl-1 inhibitor of formula (II) as described herein, and
(b) a second anticancer agent, wherein the second anticancer agent is selected from anthracyclines, cytarabine and hypomethylating agents,
to a subject in need thereof.

In another embodiment, the Mcl-1 inhibitor is (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid (Compound 1).

In another embodiment, the Mcl-1 inhibitor is (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[1-(2,2,2-trifluoroethyl)-1H-pyrazol-5-yl]methoxy}phenyl)propanoic acid (Compound 2).

BRIEF DESCRIPTION OF THE FIGURES

FIG. 6 illustrates the superior efficacy of decitabine in combination with Compound 2 (Mcl-1 inhibitor) compared to either agent alone. NRG-SG3 mice were transplanted with $10^6$ primary AML cells (AML54). Engraftment was confirmed at 6 weeks by detection of hCD45 in peripheral blood. Cohorts of mice were then treated with a) vehicle, b) Compound 2 (Mcl-1 inhibitor) 25 mg/kg IV (×2 days) c) decitabine 0.4 mg/kg/d by IP (×5 days) or d) combination of Compound 2+decitabine. Mice were euthanized on day 8 after treatment and leukemic burden assessed by flow cytometric staining of flushed femurs showing the percentage of human CD45+ cells, after indicated treatments.

DETAILED DESCRIPTION OF THE INVENTION

Figure 1:
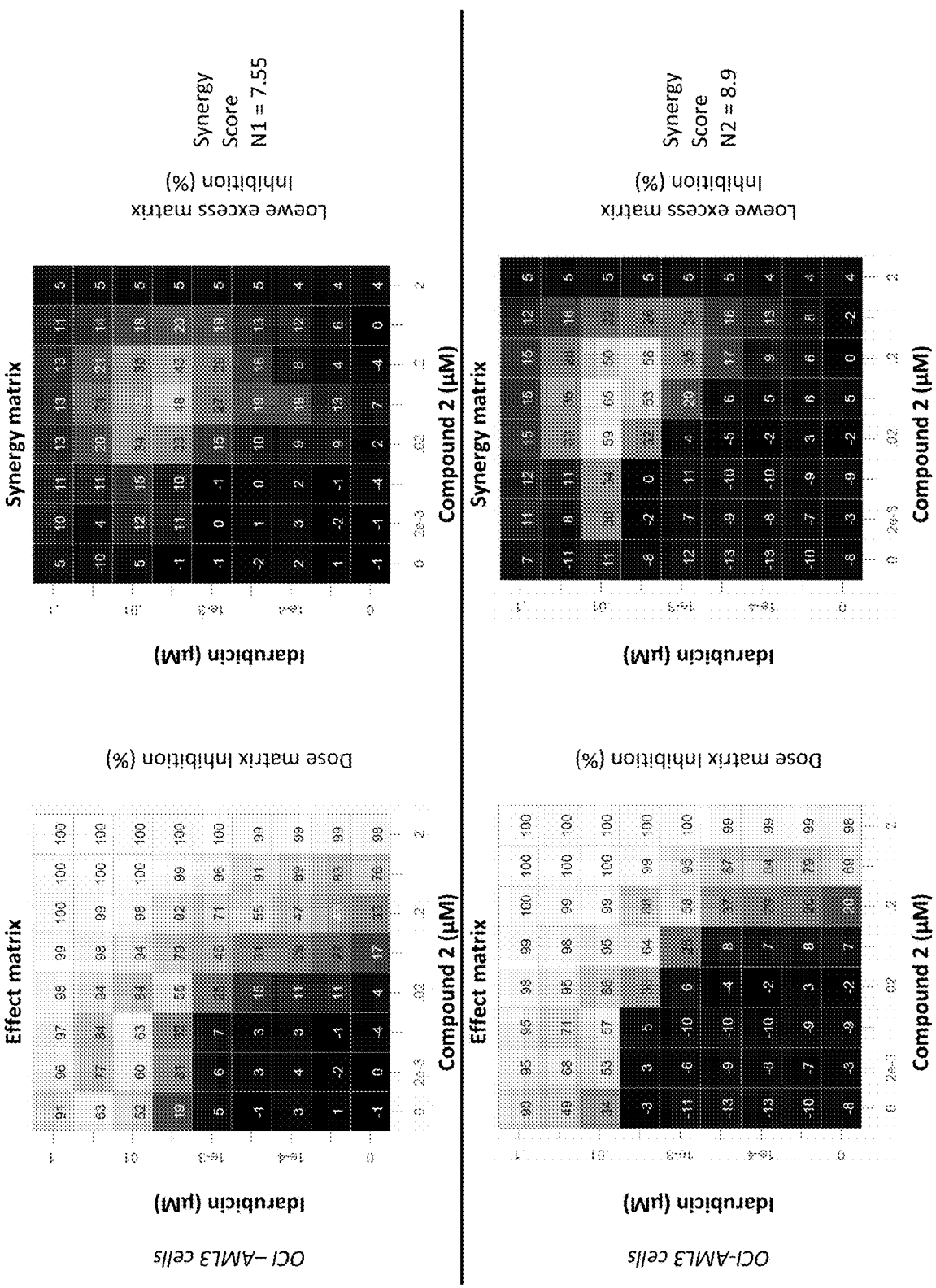
FIG. 1 illustrates an exemplary cell growth inhibition effect and synergy combination matrices for inhibition of cell growth (left) and Loewe excess inhibition (right) afforded by Compound 2 (Mcl-1 inhibitor) in combination with idarubicin in the AML cell line OCI-AML3 in two independent experiments. Values in the effect matrix range from 0 (no inhibition) to 100 (total inhibition). Values in the synergy matrix represent the extent of growth inhibition in excess of the theoretical additivity calculated based on the single agent activities of Compound 2 and idarubicin at the concentrations tested.

The invention therefore provides in Embodiment E1, a combination comprising:
(a) a Mcl-1 inhibitor of formula (I):

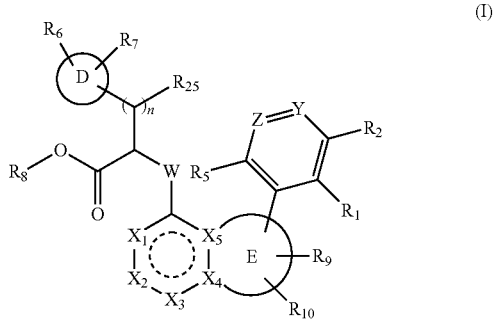

wherein:
D represents a cycloalkyl group, a heterocycloalkyl group, an aryl group or a heteroaryl group, E represents a furyl, thienyl or pyrrolyl ring, $X_1$, $X_3$, $X_4$ and $X_5$ independently of one another represent a carbon atom or a nitrogen atom, $X_2$ represents a C—$R_{26}$ group or a nitrogen atom, ◯ means that the ring is aromatic, Y represents a nitrogen atom or a C—$R_3$ group, Z represents a nitrogen atom or a C—$R_4$ group, $R_1$ represents a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl group, a hydroxy group, a hydroxy($C_1$-$C_6$)alkyl group, a linear or branched ($C_1$-$C_6$)alkoxy group, —S—($C_1$-$C_6$)alkyl group, a cyano group, a nitro group, -$Cy_8$, -alkyl($C_1$-$C_6$)—$NR_{11}R_{11}'$, —O-alkyl($C_1$-$C_6$)—$NR_{11}R_{11}'$, —O-alkyl($C_1$-$C_6$)—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl($C_1$-$C_6$)—$NR_{11}$—C(O)—$R_{11}'$, —$SO_2$—$NR_{11}R_{11}'$, or —$SO_2$-alkyl($C_1$-$C_6$), $R_2$, $R_3$, $R_4$ and $R_5$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a hydroxy($C_1$-$C_6$)alkyl group, a linear or branched ($C_1$-$C_6$)alkoxy group, a —S—($C_1$-$C_6$)alkyl group, a cyano group, a nitro group, -alkyl($C_0$-$C_6$)—$NR_{11}R_{11}'$, —O-$Cy_1$, -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$NR_{11}R_{11}'$, —O-alkyl($C_1$-$C_6$)—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl($C_1$-$C_6$)—$NR_{11}$—C(O)—$R_{11}'$, —$SO_2$—$NR_{11}R_{11}'$, or —$SO_2$-alkyl($C_1$-$C_6$), or the substituents of the pair ($R_1$, $R_2$), ($R_2$, $R_3$), ($R_3$, $R_4$), ($R_4$, $R_5$) form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by from 1 to 2 groups selected from halogen, linear or branched ($C_1$-$C_6$)alkyl, -alkyl($C_0$-$C_6$)—$NR_{11}R_{11}'$, —$NR_{13}R_{13}'$, -alkyl($C_0$-$C_6$)-$Cy_1$ or oxo, $R_6$ and $R_7$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a linear or branched ($C_1$-$C_6$)alkoxy group, a —S—($C_1$-$C_6$)alkyl group, a cyano group, a nitro group, -alkyl($C_0$-$C_6$)—$NR_{11}R_{11}'$, —O-alkyl($C_1$-$C_6$)—$NR_{11}R_{11}'$, —O-$Cy_1$, -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$R_{12}$, —C(O)—$OR_{11}$, —O—C(O)—$R_{11}$, —C(O)—$NR_{11}R_{11}'$, —$NR_{11}$—C(O)—$R_{11}'$, —$NR_{11}$—C(O)—$OR_{11}'$, -alkyl($C_1$-$C_6$)—$NR_{11}$—C(O)—$R_{11}'$, —$SO_2$—$NR_{11}R_{11}'$, or —$SO_2$-alkyl($C_1$-$C_6$), or the substituents of the pair ($R_6$, $R_7$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched ($C_1$-$C_6$)alkyl group, —$NR_{13}R_{13}'$, -alkyl($C_0$-$C_6$)-$Cy_1$ or an oxo, W represents a —$CH_2$— group, a —NH— group or an oxygen atom, $R_8$ represents a hydrogen atom, a linear or branched ($C_1$-$C_8$)alkyl group, a —$CHR_aR_b$ group, an aryl group, a heteroaryl group, an arylalkyl($C_1$-$C_6$) group, or a heteroarylalkyl($C_1$-$C_6$) group, $R_9$ represents a hydrogen atom, a linear or branched ($C_1$-$C_6$)alkyl group, a linear or branched ($C_2$-$C_6$)alkenyl group, a linear or branched ($C_2$-$C_6$)alkynyl group, -$Cy_2$, -alkyl($C_1$-$C_6$)-$Cy_2$, -alkenyl($C_2$-$C_6$)-$Cy_2$, -alkynyl($C_2$-$C_6$)-$Cy_2$, -$Cy_2$-$Cy_3$, -alkynyl($C_2$-$C_6$)—O-$Cy_2$, -$Cy_2$-alkyl($C_0$-$C_6$)—O-alkyl($C_0$-$C_6$)-$Cy_3$, a halogen atom, a cyano group, —C(O)—$R_{14}$, or —C(O)—$NR_{14}R_{14}'$, $R_{10}$ represents a hydrogen atom, a linear or branched ($C_1$-$C_6$)alkyl group, a linear or branched ($C_2$-$C_6$)alkenyl group, a linear or branched ($C_2$-$C_6$)alkynyl group, an arylalkyl($C_1$-$C_6$) group, a cycloalkylalkyl($C_1$-$C_6$) group, a linear or branched ($C_1$-$C_6$)polyhaloalkyl, or -alkyl($C_1$-$C_6$)—O-$Cy_4$, or the substituents of the pair ($R_9$, $R_{10}$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, $R_{11}$ and $R_{11}'$ independently of one another represent a hydrogen atom, an optionally substituted linear or branched ($C_1$-$C_6$)alkyl group, or -alkyl($C_0$-$C_6$)-$Cy_1$, or the substituents of the pair ($R_{11}$, $R_{11}'$) form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the nitrogen in question may be substituted by from 1 to 2 groups representing a hydrogen atom, or a linear or branched ($C_1$-$C_6$)alkyl group and it being understood that one or more of the carbon atoms of the possible substituents, may be deuterated, $R_{12}$ represents -$Cy_5$, -$Cy_5$-alkyl($C_1$-$C_6$)—O-alkyl($C_1$-$C_6$)-$Cy_6$, -$Cy_5$-alkyl($C_1$-$C_6$)-$Cy_6$, -$Cy_5$-alkyl($C_0$-$C_6$)—$NR_{11}$-alkyl($C_0$-$C_6$)-$Cy_6$, -$Cy_5$-$Cy_6$-O-alkyl($C_0$-$C_6$)-$Cy_7$, -$Cy_5$-alkyl($C_0$-$C_6$)—O-alkyl($C_0$-$C_6$)-$Cy_9$, -$Cy_5$-alkyl($C_0$-$C_6$)-$Cy_9$, —NH—C(O)—NH—$R_{11}$, -$Cy_5$-alkyl($C_0$-$C_6$)—$NR_{11}$-alkyl($C_0$-$C_6$)-$Cy_9$, —C(O)—$NR_{11}R_{11}'$, —$NR_{11}R_{11}'$, —OR, —$NR_{11}$—C(O)—$R_{11}'$, —O-alkyl($C_1$-$C_6$)—$OR_{11}$, —$SO_2$—$R_{11}$, —C(O)—$OR_{11}$,

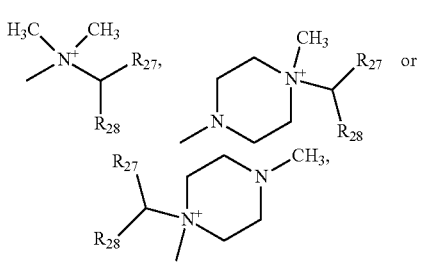

it being possible for the ammonium so defined to exist as a zwitterionic form or to have a monovalent anionic counterion, $R_{13}$, $R_{13}'$, $R_{14}$ and $R_{14}'$ independently of one another represent a hydrogen atom, or an optionally substituted linear or branched $(C_1-C_6)$alkyl group, $R_a$ represents a hydrogen atom or a linear or branched $(C_1-C_6)$alkyl group, $R_b$ represents a —O—C(O)—O—$R_c$ group, a —O—C(O)—N$R_c R_c'$ group, or a —O—P(O)(O$R_c$)$_2$ group, $R_c$ and $R_c'$ independently of one another represent a hydrogen atom, a linear or branched $(C_1-C_8)$alkyl group, a cycloalkyl group, a $(C_1-C_6)$alkoxy$(C_1-C_6)$alkyl group, or a $(C_1-C_6)$alkoxycarbonyl$(C_1-C_6)$alkyl group, or the substituents of the pair ($R_c$, $R_c'$) form together with the nitrogen atom carrying them a non-aromatic ring composed of from 5 to 7 ring members, which may contain in addition to the nitrogen atom from 1 to 3 heteroatoms selected from oxygen and nitrogen, it being understood that the nitrogen in question may be substituted by a group representing a linear or branched $(C_1-C_6)$alkyl group, $Cy_1$, $Cy_2$, $Cy_3$, $Cy_4$, $Cy_5$, $Cy_6$, $Cy_7$, $Cy_8$ and $Cy_{10}$ independently of one another, represent a cycloalkyl group, a heterocycloalkyl group, an aryl group or a heteroaryl group, $Cy_9$ represents

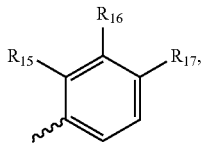

or $Cy_9$ represents a heteroaryl group which is substituted by a group selected from —O—P(O)(O$R_{20}$)$_2$; —O—P(O)(O$^-$M$^+$)$_2$; —(CH$_2$)$_p$—O—(CHR$_{18}$—CHR$_{19}$—O)$_q$—R$_{20}$; hydroxy; hydroxy$(C_1-C_6)$alkyl; —(CH$_2$)$_r$—U—(CH$_2$)$_s$-heterocycloalkyl; or —U—(CH$_2$)$_q$—NR$_{21}$R$_{21}'$, $R_{15}$ represents a hydrogen atom; a —(CH$_2$)$_p$—O—(CHR$_{18}$—CHR$_{19}$—O)$_q$—R$_{20}$ group; a linear or branched $(C_1-C_6)$alkoxy$(C_1-C_6)$alkyl group; a —U—(CH$_2$)$_q$—NR$_{21}$R$_{21}'$ group; or a —(CH$_2$)$_r$—U—(CH$_2$)$_s$-heterocycloalkyl group, $R_{16}$ represents a hydrogen atom; a hydroxy group; a hydroxy$(C_1-C_6)$alkyl group; a —(CH$_2$)$_r$—U—(CH$_2$)$_s$-heterocycloalkyl group; a (CH$_2$)$_r$—U—V—O—P(O)(OR$_{20}$)$_2$ group; a —O—P(O)(O$^-$M$^+$)$_2$ group; a —(CH$_2$)$_p$—O—(CHR$_{18}$—CHR$_{19}$—O)$_q$—R$_{20}$ group; a —(CH$_2$)$_p$—O—C(O)—NR$_{22}$R$_{23}$ group; or a —U—(CH$_2$)$_q$—NR$_{21}$R$_{21}'$ group, $R_{17}$ represents a hydrogen atom; a —(CH$_2$)$_p$—O—(CHR$_{18}$—CHR$_{19}$—O)$_q$—R$_{20}$ group; a —O—P(O)(OR$_{20}$)$_2$ group; a —O—P(O)(O$^-$M$^+$)$_2$ group; a hydroxy group; a hydroxy$(C_1-C_6)$alkyl group; a —(CH$_2$)$_r$—U—(CH$_2$)$_s$-heterocycloalkyl group; a —U—(CH$_2$)$_q$—NR$_{21}$R$_{21}'$ group; or an aldonic acid, M$^+$ represents a pharmaceutically acceptable monovalent cation, U represents a bond or an oxygen atom, V represents a —(CH$_2$)$_s$— group or a —C(O)— group, $R_{18}$ represents a hydrogen atom or a $(C_1-C_6)$alkoxy$(C_1-C_6)$alkyl group, $R_{19}$ represents a hydrogen atom or a hydroxy$(C_1-C_6)$alkyl group, $R_{20}$ represents a hydrogen atom or a linear or branched $(C_1-C_6)$alkyl group, $R_{21}$ and $R_{21}'$ independently of one another represent a hydrogen atom, a linear or branched $(C_1-C_6)$alkyl group, or a hydroxy$(C_1-C_6)$alkyl group, or the substituents of the pair ($R_{21}$, $R_{21}'$) form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the resulting ring may be substituted by a group representing a hydrogen atom or a linear or branched $(C_1-C_6)$alkyl group, $R_{22}$ represents a $(C_1-C_6)$alkoxy$(C_1-C_6)$alkyl group, a —(CH$_2$)$_p$—NR$_{24}$R$_{24}'$ group, or a —(CH$_2$)$_p$—O—(CHR$_{18}$—CHR$_{19}$—O)—R$_{20}$ group, $R_{23}$ represents a hydrogen atom or a $(C_1-C_6)$alkoxy$(C_1-C_6)$alkyl group, or the substituents of the pair ($R_{22}$, $R_{23}$) form together with the nitrogen atom carrying them an aromatic or non-aromatic ring composed of from 5 to 18 ring members, which may contain in addition to the nitrogen atom from 1 to 5 heteroatoms selected from oxygen, sulphur and nitrogen, it being understood that the resulting ring may be substituted by a group representing a hydrogen atom, a linear or branched $(C_1-C_6)$alkyl group or a heterocycloalkyl group, $R_{24}$ and $R_{24}'$ independently of one another represent a hydrogen atom or a linear or branched $(C_1-C_6)$alkyl group, or the substituents of the pair ($R_{24}$, $R_{24}'$) form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the resulting ring may be substituted by a group representing a hydrogen atom or a linear or branched $(C_1-C_6)$alkyl group, $R_{25}$ represents a hydrogen atom, a hydroxy group, or a hydroxy$(C_1-C_6)$alkyl group, $R_{26}$ represents a hydrogen atom, a halogen atom, a linear or branched $(C_1-C_6)$alkyl group, or a cyano group, $R_{27}$ represents a hydrogen atom or a linear or branched $(C_1-C_6)$alkyl group, $R_{28}$ represents a —O—P(O)(O$^-$)(O$^-$) group, a —O—P(O)(O$^-$)(OR$_{30}$) group, a —O—P(O)(OR$_{30}$)(OR$_{30}'$) group, a —O—SO$_2$—O$^-$ group, a —O—SO$_2$—OR$_{30}$ group, -Cy$_{10}$, a —O—C(O)—R$_{29}$ group, a —O—C(O)—OR$_{29}$ group or a —O—C(O)—NR$_{29}$R$_{29}'$ group;

$R_{29}$ and $R_{29}'$ independently of one another represent a hydrogen atom, a linear or branched $(C_1-C_6)$alkyl group or a linear or branched amino$(C_1-C_6)$alkyl group, $R_{30}$ and $R_{30}'$ independently of one another represent a hydrogen atom, a linear or branched $(C_1-C_6)$alkyl group or an arylalkyl$(C_1-C_6)$ group, n is an integer equal to 0 or 1, p is an integer equal to 0, 1 or 2, q is an integer equal to 1, 2, 3 or 4, r and s are independently an integer equal to 0 or 1, it being understood that:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, it being possible for the aryl, heteroaryl, cycloalkyl and heterocycloalkyl groups so defined and the alkyl, alkenyl, alkynyl, alkoxy, to be substituted by from 1 to 4 groups selected from optionally substituted linear or branched ($C_1$-$C_6$)alkyl, optionally substituted linear or branched ($C_2$-$C_6$) alkenyl group, optionally substituted linear or branched ($C_2$-$C_6$)alkynyl group, optionally substituted linear or branched ($C_1$-$C_6$)alkoxy, optionally substituted ($C_1$-$C_6$)alkyl-S—, hydroxy, oxo (or N-oxide where appropriate), nitro, cyano, —C(O)—OR', —O—C(O)—R', —C(O)—NR'R", —NR'R", —(C=NR')—OR", linear or branched ($C_1$-$C_6$) polyhaloalkyl, trifluoromethoxy, or halogen, it being understood that R' and R" independently of one another represent a hydrogen atom or an optionally substituted linear or branched ($C_1$-$C_6$)alkyl group, and it being understood that one or more of the carbon atoms of the preceding possible substituents, may be deuterated, or their enantiomers, diastereoisomers, atropisomers, or addition salts thereof with a pharmaceutically acceptable acid or base, and (b) a second anticancer agent, wherein the second anticancer agent is selected anthracyclines, cytarabine and hypomethylating agents, for simultaneous, sequential or separate use.

Further enumerated embodiments (E) of the invention are described herein. It will be recognized that features specified in each embodiment may be combined with other specified features to provide further embodiments of the present invention.

E2. A combination according to E1, comprising:
(a) a Mcl-1 inhibitor of formula (II), a particular case of Mcl-1 inhibitor of formula (I):

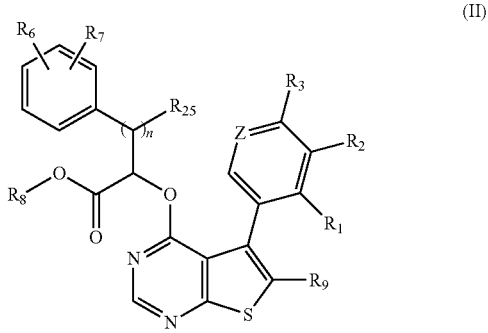

(II)

wherein:
Z represents a nitrogen atom or a C—$R_4$ group,
$R_1$ represents a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)alkoxy group, —S—($C_1$-$C_6$)alkyl group, a linear or branched ($C_1$-$C_6$)polyhaloalkyl, a hydroxy group, a cyano, —N$R_{11}R_{11}$', -$Cy_8$ or a halogen atom,
$R_2$, $R_3$ and $R_4$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a linear or branched ($C_1$-$C_6$)alkoxy group, —S—($C_1$-$C_6$)alkyl group, a cyano group, a nitro group, -alkyl($C_0$-$C_6$)—$NR_{11}R_{11}$', —O-$Cy_1$, -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$R_{12}$, —C(O)—$OR_{11}$, —O—C(O)—$R_{11}$, —C(O)—$NR_{11}R_{11}$', —$NR_{11}$—C(O)—$R_{11}$', —$NR_{11}$—C(O)—$OR_{11}$', -alkyl($C_1$-$C_6$)—$NR_{11}$—C(O)—$R_{11}$', —$SO_2$—$NR_{11}R_{11}$', or —$SO_2$-alkyl($C_1$-$C_6$),
or the substituents of one of the pairs ($R_2$, $R_3$), ($R_3$, $R_4$) form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched ($C_1$-$C_6$)alkyl group, —$NR_{13}R_{13}$', -alkyl($C_0$-$C_6$)-$Cy_1$ or an oxo,
$R_6$ and $R_7$ independently of one another represent a hydrogen atom, a halogen atom, a linear or branched ($C_1$-$C_6$)alkyl group, a linear or branched ($C_2$-$C_6$)alkenyl group, a linear or branched ($C_2$-$C_6$)alkynyl group, a linear or branched ($C_1$-$C_6$)polyhaloalkyl, a hydroxy group, a linear or branched ($C_1$-$C_6$)alkoxy group, a —S—($C_1$-$C_6$)alkyl group, a cyano group, a nitro group, -alkyl($C_0$-$C_6$)—$NR_{11}R_{11}$', —O-$Cy_1$, -alkyl($C_0$-$C_6$)-$Cy_1$, -alkenyl($C_2$-$C_6$)-$Cy_1$, -alkynyl($C_2$-$C_6$)-$Cy_1$, —O-alkyl($C_1$-$C_6$)—$R_{12}$, —C(O)—$OR_{11}$, —O—C(O)—$R_{11}$, —C(O)—$NR_{11}R_{11}$', —$NR_{11}$—C(O)—$R_{11}$', —$NR_{11}$—C(O)—$OR_{11}$', -alkyl($C_1$-$C_6$)—$NR_{11}$—C(O)—$R_{11}$', —$SO_2$—$NR_{11}R_{11}$', or —$SO_2$-alkyl($C_1$-$C_6$),
or the substituents of the pair ($R_6$, $R_7$), when grafted onto two adjacent carbon atoms, form together with the carbon atoms carrying them an aromatic or non-aromatic ring composed of from 5 to 7 ring members, which may contain from 1 to 3 heteroatoms selected from oxygen, sulphur and nitrogen, it being understood that resulting ring may be substituted by a group selected from a linear or branched ($C_1$-$C_6$)alkyl group, —$NR_{13}R_{13}$', -alkyl($C_0$-$C_6$)-$Cy_1$ or an oxo,
$R_8$ represents a hydrogen atom, a linear or branched ($C_1$-$C_8$)alkyl group, an aryl group, a heteroaryl group, an arylalkyl($C_1$-$C_6$) group, or a heteroarylalkyl($C_1$-$C_6$) group,
$R_9$ represents a linear or branched ($C_1$-$C_6$)alkyl group, a linear or branched ($C_2$-$C_6$)alkenyl group, a linear or branched ($C_2$-$C_6$)alkynyl group, -$Cy_2$, -alkyl($C_1$-$C_6$)-$Cy_2$, -alkenyl($C_2$-$C_6$)-$Cy_2$, -alkynyl($C_2$-$C_6$)-$Cy_2$, -$Cy_2$-$Cy_3$, -alkynyl($C_2$-$C_6$)—O-$Cy_2$, -$Cy_2$-alkyl($C_0$-$C_6$)—O-alkyl($C_0$-$C_6$)-$Cy_3$, a halogen atom, a cyano group, —C(O)—$R_{14}$, or —C(O)—$NR_{14}R_{14'}$,
$R_{11}$ and $R_{11}$' independently of one another represent a hydrogen atom, an optionally substituted linear or branched ($C_1$-$C_6$)alkyl group, or -alkyl($C_0$-$C_6$)-$Cy_1$,
or the substituents of the pair ($R_{11}$, $R_{11}$') form together with the nitrogen atom carrying them an aromatic or non-aromatic ring composed of from 5 to 7 ring members, which may contain in addition to the nitrogen atom from 1 to 3 heteroatoms selected from oxygen, sulphur and nitrogen, it being understood that the nitrogen in question may be substituted by a group representing a hydrogen atom, or a linear or branched ($C_1$-$C_6$)alkyl group and it being understood that one or more of the carbon atoms of the possible substituents, may be deuterated,
$R_{12}$ represents -$Cy_5$, -$Cy_5$-alkyl($C_0$-$C_6$)-$Cy_6$, -$Cy_5$-alkyl ($C_0$-$C_6$)—O-alkyl($C_0$-$C_6$)-$Cy_6$, -$Cy_5$-alkyl($C_0$-$C_6$)—

NR₁₁-alkyl(C₀-C₆)-Cy₆, -Cy₅-Cy₆-O-alkyl(C₀-C₆)-Cy₇, —C(O)—NR₁₁R₁₁', —NR₁₁R₁₁', —OR₁₁, —NR₁₁—C(O)—R₁₁', —O-alkyl(C₁-C₆)—OR₁₁, —SO₂—R₁, —C(O)—OR₁₁, or —NH—C(O)—NH—R₁₁, R₁₃, R₁₃', R₁₄ and R₁₄' independently of one another represent a hydrogen atom, or an optionally substituted linear or branched (C₁-C₆)alkyl group, R₂₅ represents a hydrogen atom, a hydroxy group, or a hydroxy(C₁-C₆)alkyl group, Cy₁, Cy₂, Cy₃, Cy₅, Cy₆, Cy₇ and Cy₈ independently of one another, represent a cycloalkyl group, a heterocycloalkyl group, an aryl group or a heteroaryl group, n is an integer equal to 0 or 1, it being understood that:

"aryl" means a phenyl, naphthyl, biphenyl, indanyl or indenyl group,

"heteroaryl" means any mono- or bi-cyclic group composed of from 5 to 10 ring members, having at least one aromatic moiety and containing from 1 to 3 heteroatoms selected from oxygen, sulphur and nitrogen, "cycloalkyl" means any mono- or bi-cyclic non-aromatic carbocyclic group containing from 3 to 10 ring members, "heterocycloalkyl" means any mono- or bi-cyclic non-aromatic carbocyclic group containing from 3 to 10 ring members, and containing from 1 to 3 heteroatoms selected from oxygen, sulphur and nitrogen, which may include fused, bridged or spiro ring systems, it being possible for the aryl, heteroaryl, cycloalkyl and heterocycloalkyl groups so defined and the alkyl, alkenyl, alkynyl, alkoxy, to be substituted by from 1 to 4 groups selected from optionally substituted linear or branched (C₁-C₆)alkyl, optionally substituted linear or branched (C₂-C₆) alkenyl group, optionally substituted linear or branched (C₂-C₆)alkynyl group, optionally substituted linear or branched (C₁-C₆)alkoxy, optionally substituted (C₁-C₆)alkyl-S—, hydroxy, oxo (or N-oxide where appropriate), nitro, cyano, —C(O)—OR', —O—C(O)—R', —C(O)—NR'R", —NR'R", —(C=NR')—OR", linear or branched (C₁-C₆) polyhaloalkyl, trifluoromethoxy, or halogen, it being understood that R' and R" independently of one another represent a hydrogen atom or an optionally substituted linear or branched (C₁-C₆)alkyl group, and it being understood that one or more of the carbon atoms of the preceding possible substituents, may be deuterated, or their enantiomers, diastereoisomers, atropisomers, or addition salts thereof with a pharmaceutically acceptable acid or base, and (b) a second anticancer agent, wherein the second anticancer agent is selected from anthracyclines, cytarabine and hypomethylating agents, for simultaneous, sequential or separate use.

E3. A combination according to E1 or E2, wherein the second anticancer agent is an anthracycline selected from idarubicin, daunorubicin and mitoxantrone, more particularly, idarubicin and daunorubicin, even more particularly, idarubicin.

E4. A combination according to E1 or E2, wherein the second anticancer agent is a hypomethylating agent selected from decitabine, azacitidine and guadecitabine, more particularly, decitabine and azacitidine, even more particularly, decitabine.

E5. A combination according to E1 or E2, wherein the second anticancer agent is selected from idarubicin, daunorubicin, cytarabine, decitabine and azacitidine.

E6. A combination according to E1 or E2, wherein the second anticancer agent is idarubicin.

E7. A combination according to E1 or E2, wherein the second anticancer agent is cytarabine.

E8. A combination according to E1 or E2, wherein the second anticancer agent is decitabine.

E9. A combination according to E1 or E2, wherein the second anticancer agent is azacitidine.

E10. A combination according to any of E1 to E9, wherein the Mcl-1 inhibitor is (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[1-(2,2,2-trifluoroethyl)-1H-pyrazol-5-yl]methoxy}phenyl) propanoic acid.

E11. A combination according to any of E1 to E9, wherein the Mcl-1 inhibitor is (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-[{2-(2-methoxyphenyl)pyrimidin-4-yl]methoxy}phenyl)propanoic acid.

E12. A combination according to E1 or E2, comprising:
(a) a Mcl-1 inhibitor selected from (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[1-(2,2,2-trifluoroethyl)-1H-pyrazol-5-yl]methoxy}phenyl)propanoic acid or (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid, and
(b) a second anticancer agent, wherein the second anticancer agent is selected from idarubicin, cytarabine, decitabine and azacitidine,
for simultaneous, sequential or separate use.

E13. A combination according to E1 or E12, wherein the dose of (2R)-2-{[(5S$_a$)-5-{3-chloro-2-methyl-4-[2-(4-methylpiperazin-1-yl)ethoxy]phenyl}-6-(4-fluorophenyl) thieno[2,3-d]pyrimidin-4-yl]oxy}-3-(2-{[2-(2-methoxyphenyl)pyrimidin-4-yl]methoxy}phenyl)propanoic acid during the combination treatment is from 25 mg to 1500 mg.

E14. A combination according to E1, E12 or E13, wherein (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoic acid is administered during the combination treatment once a week.

E15. A combination according to any of E1 to E14, wherein the Mcl-1 inhibitor is administered orally.

E16. A combination according to any of E1 to E14, wherein the Mcl-1 inhibitor is administered intravenously.

E17. A combination according to any of E1 to E16, for use in the treatment of cancer.

E18. A combination according to E17 wherein the cancer is acute myeloid leukemia.

E19. A combination according to E17 wherein the cancer is acute lymphocytic leukemia.

E20. The combination for use according to any of E17 to E19, wherein the Mcl-1 inhibitor and the second anticancer agent are provided in amounts which are jointly therapeutically effective for the treatment of cancer.

E21. The combination for use according to E20, wherein the Mcl-1 inhibitor and the second anticancer agent are provided in amounts which are synergistically effective for the treatment of cancer.

E22. The combination for use according to E21, wherein the Mcl-1 inhibitor and the second anticancer agent are provided in synergistically effective amounts which enable a reduction of the dose required for each compound in the treatment of cancer, whilst providing an efficacious cancer treatment, with eventually a reduction in side effects.

E23. A combination according to any of E1 to E16, for use in the treatment of acute myeloid leukemia in patients who achieve remission.

E24. A combination according to any of E1 to E23, further comprising one or more excipients.

E25. A combination according to E1, further comprising a third anticancer agent.

E26. A combination according to E25 wherein the second anticancer agent is cytarabine and the third anticancer agent is daunorubicin or idarubicin.

E27. The use of a combination according to any of E1 to E26, in the manufacture of a medicament for the treatment of cancer.

E28. The use according to E27, wherein the cancer is acute myeloid leukemia.

E29. The use according to E27, wherein the cancer is acute lymphocytic leukemia.

E30. A medicament containing, separately or together,
(a) a Mcl-1 inhibitor of formula (I) as defined in E1, and
(b) a second anticancer agent, wherein the second anticancer agent is selected from anthracyclines, cytarabine and hypomethylating agents,
for simultaneous, sequential or separate administration, and wherein the Mcl-1 inhibitor and the second anticancer agent are provided in effective amounts for the treatment of cancer.

E31. A medicament containing, separately or together,
(a) a Mcl-1 inhibitor of formula (II) as defined in E2, and
(b) a second anticancer agent, wherein the second anticancer agent is selected from anthracyclines, cytarabine and hypomethylating agents,
for simultaneous, sequential or separate administration, and wherein the Mcl-1 inhibitor and the second anticancer agent are provided in effective amounts for the treatment of cancer.

E32. The medicament according to E30 or E31, wherein the second anticancer agent is selected from idarubicin, daunorubicin, cytarabine, decitabine and azacitidine.

E33. A method of treating cancer, comprising administering a jointly therapeutically effective amount of:
(a) a Mcl-1 inhibitor of formula (I) as defined in E1, and
(b) a second anticancer agent, wherein the second anticancer agent is selected from anthracyclines, cytarabine and hypomethylating agents,
to a subject in need thereof.

E34. A method of treating cancer, comprising administering a jointly therapeutically effective amount of:
(a) a Mcl-1 inhibitor of formula (II) as defined in E2, and
(b) a second anticancer agent, wherein the second anticancer agent is selected from anthracyclines, cytarabine and hypomethylating agents,
to a subject in need thereof.

E35. The method according to E33 or E34, wherein the second anticancer agent is selected from idarubicin, daunorubicin, cytarabine, decitabine and azacitidine.

E36. A method according to E33 or E34 wherein the Mcl-1 inhibitor of formula (I) is (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid.

E37. A method for sensitizing a patient who is (i) refractory to at least one chemotherapy treatment, or (ii) in relapse after treatment with chemotherapy, or both (i) and (ii), wherein the method comprises administering a jointly therapeutically effective amount of Mcl-1 inhibitor of formula (I) as defined in E1 in combination with a second anticancer agent, as described herein, to said patient.

E38. A method for sensitizing a patient who is (i) refractory to at least one chemotherapy treatment, or (ii) in relapse after treatment with chemotherapy, or both (i) and (ii), wherein the method comprises administering a jointly therapeutically effective amount of Mcl-1 inhibitor of formula (II) as defined in E2 in combination with a second anticancer agent, as described herein, to said patient.

'Combination' refers to either a fixed dose combination in one unit dosage form (e.g., capsule, tablet, or sachet), non-fixed dose combination, or a kit of parts for the combined administration where a compound of the present invention and one or more combination partners (e.g. another drug as explained below, also referred to as 'therapeutic agent' or 'co-agent') may be administered independently at the same time or separately within time intervals, especially where these time intervals allow that the combination partners show a cooperative, e.g. synergistic effect.

The terms 'co-administration' or 'combined administration' or the like as utilized herein are meant to encompass administration of the selected combination partner to a single subject in need thereof (e.g. a patient), and are intended to include treatment regimens in which the agents are not necessarily administered by the same route of administration or at the same time.

The term 'fixed dose combination' means that the active ingredients, e.g. a compound of formula (I) and one or more combination partners, are both administered to a patient simultaneously in the form of a single entity or dosage.

The term 'non-fixed dose combination' means that the active ingredients, e.g. a compound of the present invention and one or more combination partners, are both administered to a patient as separate entities either simultaneously or sequentially, with no specific time limits, wherein such administration provides therapeutically effective levels of the two compounds in the body of the patient. The latter also applies to cocktail therapy, e.g. the administration of three or more active ingredients.

'Cancer' means a class of disease in which a group of cells display uncontrolled growth. Cancer types include hematologic cancers including acute myeloid leukemia, myelodysplastic syndromes, acute lymphocytic leukemia and lymphoma. Cancer types also include solid tumors including carcinoma, sarcoma, or blastoma.

The term 'jointly therapeutically effective' means that the therapeutic agents may be given separately (in a chronologically staggered manner, especially a sequence-specific manner) in such time intervals that they prefer, in the warm-blooded animal, especially human, to be treated, still show a (preferably synergistic) interaction (joint therapeutic effect).

Whether this is the case can, inter alia, be determined by following the blood levels, showing that both compounds are present in the blood of the human to be treated at least during certain time intervals.

'Standard-of-care drug' or 'standard-of-care chemotherapy' means idarubicin, daunorubicin, mitoxantrone, cytarabine, decitabine, guadecitabine or azacitidine.

Particularly, 'standard-of-care drug' or 'standard-of-care' chemotherapy means idarubicin, daunorubicin, cytarabine, decitabine or azacitidine.

'Synergistically effective' or 'synergy' means that the therapeutic effect observed following administration of two or more agents is greater than the sum of the therapeutic effects observed following the administration of each single agent.

As used herein, the term 'treat', 'treating' or 'treatment' of any disease or disorder refers in one embodiment, to ameliorating the disease or disorder (i.e., slowing or arresting or reducing the development of the disease or at least one of the clinical symptoms thereof).

In another embodiment 'treat', 'treating' or 'treatment' refers to alleviating or ameliorating at least one physical parameter including those which may not be discernible by the patient. In yet another embodiment, 'treat', 'treating' or 'treatment' refers to modulating the disease or disorder, either physically, (e.g., stabilization of a discernible symptom), physiologically, (e.g., stabilization of a physical parameter), or both.

As used herein, a subject is 'in need of' a treatment if such subject would benefit biologically, medically or in quality of life from such treatment.

The term 'remission' refers to a decrease in or disappearance of signs and symptoms of cancer.

In another aspect, provided is a method for sensitizing a human who is (i) refractory to at least one chemotherapy treatment, or (ii) in relapse after treatment with chemotherapy, or both (i) and (ii), wherein the method comprises administering a Mcl-1 inhibitor of formula (I) in combination with a second anticancer agent, as described herein, to the patient. A patient who is sensitized is a patient who is responsive to the treatment involving administration of a Mcl-1 inhibitor of formula (I) in combination with a second anticancer agent, as described herein, or who has not developed resistance to such treatment.

'Medicament' means a pharmaceutical composition, or a combination of several pharmaceutical compositions, which contains one or more active ingredients in the presence of one or more excipients.

'AML' means acute myeloid leukemia.

'ALL' means acute lymphocytic leukemia.

In the pharmaceutical compositions according to the invention, the proportion of active ingredients by weight (weight of active ingredients over the total weight of the composition) is from 5 to 50%.

Among the pharmaceutical compositions according to the invention there will be more especially used those which are suitable for administration by the oral, parenteral and especially intravenous, per- or trans-cutaneous, nasal, rectal, perlingual, ocular or respiratory route, more specifically tablets, dragées, sublingual tablets, hard gelatin capsules, glossettes, capsules, lozenges, injectable preparations, aerosols, eye or nose drops, suppositories, creams, ointments, dermal gels etc.

The pharmaceutical compositions according to the invention comprise one or more excipients or carriers selected from diluents, lubricants, binders, disintegration agents, stabilisers, preservatives, absorbents, colorants, sweeteners, flavourings etc.

By Way of Non-Limiting Example there May be Mentioned:
as diluents: lactose, dextrose, sucrose, mannitol, sorbitol, cellulose, glycerol,
as lubricants: silica, talc, stearic acid and its magnesium and calcium salts, polyethylene glycol,
as binders: magnesium aluminium silicate, starch, gelatin, tragacanth, methylcellulose, sodium carboxymethylcellulose and polyvinylpyrrolidone,
as disintegrants: agar, alginic acid and its sodium salt, effervescent mixtures.

The compounds of the combination may be administered simultaneously or sequentially. The administration route is preferably the intravenous infusion or injection, and the corresponding pharmaceutical compositions may allow the instantaneous or delayed release of the active ingredients. The compounds of the combination may moreover be administered in the form of two separate pharmaceutical compositions, each containing one of the active ingredients, or in the form of a single pharmaceutical composition, in which the active ingredients are in admixture.

The useful dosage regimen varies according to the sex, age and weight of the patient, the administration route, the nature of the cancer and of any associated treatments and ranges from 25 mg to 1500 mg of Mcl-1 inhibitor per week, more preferably from 50 mg to 1400 mg per week. The dose of the second anticancer agent, as described herein, will be the same as that used when it is administered on its own.

PHARMACOLOGICAL DATA

Example 1: In Vitro Effect on Proliferation of Combining MCL-1 Inhibitors with Idarubicin, Cytarabine and Decitabine in Acute Myeloid Leukemia (AML) Cell Lines Material and Method Cell lines were sourced and maintained in the basic media supplemented with FBS as indicated in Table 1. In addition, all media contained penicillin (100 IU/mL), streptomycin (100 µg/mL) and L-glutamine (2 mM).

Cell lines were cultured at 37° C. in a humidified atmosphere containing 5% $CO_2$ and expanded in T-150 flasks. In all cases cells were thawed from frozen stocks, expanded through ≥1 passage using appropriate dilutions, counted and assessed for viability using a CASY cell counter prior to plating 150 µL/well at the densities indicated in Table 1 into 96-well plates. All cell lines were determined to be free of mycoplasma contamination in-house. Stock solutions of compounds were prepared at a concentration of 5 mM in DMSO and stored at −20° C.

In order to analyse the activity of the compounds as single agents, cells were seeded and treated with nine 2-fold serial dilutions of each compound dispensed individually directly into the cell assay plates. Effects of the compounds on cell viability were assessed after 3 days of incubation at 37° C./5% $CO_2$ by quantification of cellular ATP levels using CellTiterGlo at 75 µL reagent/well. All the experiments were performed in triplicates. Luminescence was quantified on a multipurpose plate reader. Single agent $IC_{50}$s were calculated using standard four-parametric curve fitting. $IC_{50}$ is defined as the compound concentration at which the CTG signal is reduced to 50% of that measured for the vehicle (DMSO) control (Table 2).

In order to analyse the activity of the compounds in combination with cytarabine (Table 3), idarubicin (Table 4) and decitabine (Table 5), cells were seeded and treated with seven or eight 3.16-fold serial dilutions of each compound dispensed, either individually or in all possible permutations in a checkerboard fashion, directly into the cell assay plates as indicated in FIG. 1. Effects of the single agents as well as their checkerboard combinations on cell viability were assessed after 3 days of incubation at 37° C./5% $CO_2$ by quantification of cellular ATP levels using CellTiterGlo at 75 µL reagent/well. Two independent experiments, each one performed in duplicates, were performed. Luminescence was quantified on a multipurpose plate reader.

Potential synergistic interactions between compound combinations were assessed using the Excess Inhibition 2D matrix according to the Loewe additivity model and are reported as Synergy Score (Lehar et al., *Nature Biotechnology* 2009, 27(7), 659-66). All calculations were performed using Chalice™ Bioinformatics Software available in Horizon website.

The doubling time indicated in Table 1 is the mean of the doubling time obtained in the different passages (in T-150 flasks) performed from the thawing of the cells to their seeding in the 96-well plates.

Synergy Score
SS~0→Additive
SS≥1→Weak Synergy
SS≥2→Synergy

TABLE 1

Identity and assay conditions for the 13 AML cell lines used in the combination experiments.

| Cell line | Medium | % FBS | Source | Doubling time (hours) | Cell number seeded/well |
|---|---|---|---|---|---|
| MV4; 11 | RPMI | 10 | ATCC Cat# CRL-9591 | 31.0 | 56520 |
| MOLM-13 | RPMI | 10 | DSMZ Cat# ACC554 | 32.4 | 56520 |
| PL-21 | RPMI | 10 | DSMZ Cat# ACC536 | 32.4 | 56520 |
| ML-2 | RPMI | 10 | DSMZ Cat# ACC15 | 31.6 | 56520 |
| Nomo-1 | RPMI | 10 | DSMZ Cat# ACC552 | 43.5 | 56520 |
| THP-1 | RPMI | 10 | ATCC Cat# TIB-202 | 49.6 | 56520 |
| HL-60 | IMDM | 20 | ATCC Cat# CCL240 | 34.8 | 56520 |
| Kasumi-1 | RPMI | 20 | ATCC Cat# CRL2724 | 59.4 | 56520 |
| OCI-AML3 | MEM alpha | 20 | DSMZ Cat# ACC582 | 25.7 | 56520 |
| EOL-1 | RPMI | 10 | DSMZ Cat# ACC386 | 37.6 | 113040 |
| GDM-1 | RPMI | 10 | ATCC Cat# CRL2627 | 31.6 | 56520 |
| KG1 | IMDM | 20 | ATCC Cat# CCL246 | 45.7 | 56520 |
| KG1a | IMDM | 20 | ATCC Cat# CCL246.1 | 36.5 | 56520 |

TABLE 2

Single agent $IC_{50}$ values for Compound 1, Compound 2, cytarabine, idarubicin and decitabine in 13 AML cell lines are indicated.

| | Compound 1 | | Compound 2 | | Cytarabine | | Idarubicin | | Decitabine | |
|---|---|---|---|---|---|---|---|---|---|---|
| Cell Line | Start conc [µM] | $IC_{50}$ [µM] | Start conc [µM] | $IC_{50}$ [µM] | Start conc [µM] | $IC_{50}$ [µM] | Start conc [µM] | $IC_{50}$ [µM] | Start conc [µM] | $IC_{50}$ [µM] |
| MV4; 11 | 0.01 | 0.001 | 0.01 | 0.001 | 2.0 | 0.14 | 0.1 | 0.001 | 5.0 | 0.4 |
| MOLM-13 | 0.01 | 0.002 | 0.10 | 0.004 | 2.0 | 0.19 | 0.1 | 0.003 | 5.0 | 0.4 |
| PL-21 | 0.10 | 0.065 | 2.00 | 0.238 | 2.0 | 0.10 | 2.0 | 0.023 | 5.0 | >5 |
| ML-2 | 0.10 | 0.005 | 0.10 | 0.022 | 0.1 | 0.03 | 0.1 | 0.010 | 40.0 | 14.0 |
| Nomo-1 | 0.05 | 0.013 | 0.05 | 0.022 | 2.0 | 0.99 | 0.1 | 0.028 | 5.0 | >5 |
| THP-1 | 0.10 | 0.017 | 2.00 | 0.051 | 2.0 | >2 | 0.1 | 0.024 | 30.0 | >30 |
| HL-60 | 0.10 | 0.025 | 2.00 | 0.086 | 2.0 | 0.74 | 0.1 | 0.002 | 30.0 | 14.0 |
| Kasumi-1 | 2.00 | 0.033 | 2.00 | 0.066 | 2.0 | 1.02 | 0.1 | 0.003 | 30.0 | 5.5 |
| OCI-AML3 | 2.00 | 0.146 | 2.00 | 0.340 | 2.0 | >2 | 0.1 | 0.020 | 30.0 | 8.0 |
| EOL-1 | 0.10 | 0.001 | 0.10 | 0.002 | 2.0 | 0.09 | 0.1 | 0.002 | 5.0 | 0.49 |
| GDM-1 | 0.10 | 0.008 | 0.10 | 0.027 | 0.1 | 0.03 | 0.1 | 0.008 | 80.0 | 41.0 |
| KG1 | 30.00 | 0.390 | 2.00 | 0.413 | 2.0 | 0.17 | 0.1 | 0.006 | 30.0 | 5.8 |
| KG1a | 30.00 | 2.000 | 30.00 | 2.200 | 2.0 | 0.24 | 0.1 | 0.010 | 30.0 | 14.0 |

TABLE 3

Synergy scores for Mcl-1 inhibitors in combination with cytarabine in the indicated AML cell lines. Interactions were deemed synergistic when scores ≥2.0 where observed. Start concentrations of compounds, mean of max inhibition and the standard deviation (sd) of the synergy scores are indicated

| | | | | Combination Compound 1 + Cytarabine | | Combination Compound 2 + Cytarabine | |
|---|---|---|---|---|---|---|---|
| Cell Line | Compound 1 Start conc [µM] | Compound 2 Start conc [µM] | Cytarabine Start conc [µM] | Mean of Synergy Score | Synergy Score Error (sd) | Mean of Synergy Score | Synergy Score Error (sd) |
| MV4; 11 | 0.1 | 0.3 | 2.0 | 2.3 | 0.1 | 5.3 | 2.7 |
| MOLM-13 | 0.1 | 0.3 | 2.0 | 3.6 | 1.2 | 2.7 | 0.1 |
| PL-21 | 0.3 | 2.0 | 2.0 | 2.4 | 0.1 | 2.5 | 0.5 |

TABLE 3-continued

Synergy scores for Mcl-1 inhibitors in combination with cytarabine in the indicated AML cell lines. Interactions were deemed synergistic when scores ≥2.0 where observed. Start concentrations of compounds, mean of max inhibition and the standard deviation (sd) of the synergy scores are indicated

| Cell Line | Compound 1 Start conc [µM] | Compound 2 Start conc [µM] | Cytarabine Start conc [µM] | Combination Compound 1 + Cytarabine | | Combination Compound 2 + Cytarabine | |
|---|---|---|---|---|---|---|---|
| | | | | Mean of Synergy Score | Synergy Score Error (sd) | Mean of Synergy Score | Synergy Score Error (sd) |
| ML-2 | 0.1 | 0.3 | 2.0 | 2.7 | 0.3 | 3.2 | 0.2 |
| Nomo-1 | — | 0.3 | 2.0 | ND | ND | 2.0 | 0.3 |
| THP-1 | — | 0.3 | 2.0 | ND | ND | 0.6 | 0.4 |
| HL-60 | — | 0.3 | 2.0 | ND | ND | 1.0 | 0.0 |
| Kasumi-1 | — | 0.3 | 2.0 | ND | ND | 3.3 | 0.4 |
| OCI-AML3 | 2 | 2.0 | 2.0 | 2.7 | 0.2 | 2.9 | 0.3 |
| EOL-1 | — | 0.1 | 2.0 | ND | ND | 2.7 | 0.4 |
| GDM-1 | 0.1 | 0.3 | 2.0 | 3.1 | 0.0 | 4.2 | 0.4 |
| KG1 | — | 2.0 | 2.0 | ND | ND | 0.9 | 0.1 |
| KG1a | — | 5.0 | 2.0 | ND | ND | 1.5 | 0.5 |

TABLE 4

Synergy scores for Mcl-1 inhibitors in combination with idarubicin, in the indicated AML cell lines. Interactions were deemed synergistic when scores ≥2.0 where observed. Start concentrations of compounds, mean of max inhibition and the standard deviation (sd) of the synergy scores are indicated.

| Cell Line | Compound 1 Start conc [µM] | Compound 2 Start conc [µM] | Idarubicin Start conc [µM] | Combination Compound 1 + Idarubicin | | Combination Compound 2 + Idarubicin | |
|---|---|---|---|---|---|---|---|
| | | | | Mean of Synergy Score | Synergy Score Error (sd) | Mean of Synergy Score | Synergy Score Error (sd) |
| MV4; 11 | 0.1 | 0.3 | 0.1 | 1.0 | 0.1 | 4.9 | 0.1 |
| MOLM-13 | 0.1 | 0.3 | 0.1 | 1.6 | 1.3 | 3.4 | 0.5 |
| PL-21 | 0.3 | 2.0 | 0.1 | 1.0 | 0.1 | 1.6 | 0.6 |
| ML-2 | 0.1 | 0.3 | 0.1 | 3.7 | 0.4 | 4.7 | 0.2 |
| Nomo-1 | — | 0.3 | 0.1 | ND | ND | 2.2 | 0.0 |
| THP-1 | — | 0.3 | 0.1 | ND | ND | 1.1 | 0.3 |
| HL-60 | — | 0.3 | 0.1 | ND | ND | 1.8 | 0.3 |
| Kasumi-1 | — | 0.3 | 0.1 | ND | ND | 3.1 | 0.5 |
| OCI-AML3 | 2 | 2.0 | 0.1 | 5.5 | 0.6 | 8.2 | 1.0 |
| EOL-1 | — | 0.1 | 0.1 | ND | ND | 3.9 | 1.2 |
| GDM-1 | 0.1 | 0.3 | 0.1 | 4.0 | 1.3 | 4.7 | 1.1 |
| KG1 | — | 2.0 | 0.1 | ND | ND | 1.8 | 0.9 |
| KG1a | — | 5.0 | 0.1 | ND | ND | 1.4 | 0.4 |

TABLE 5

Synergy scores for Mcl-1 inhibitors in combination with decitabine in the indicated AML cell lines. Interactions were deemed synergistic when scores ≥2.0 where observed. Start concentrations of compounds, mean of max inhibition and the standard deviation (sd) of the synergy scores are indicated.

| Cell Line | Compound 1 Start conc [µM] | Compound 2 Start conc [µM] | Decitabine Start conc [µM] | Combination Compound 1 + Decitabine | | Combination Compound 2 + Decitabine | |
|---|---|---|---|---|---|---|---|
| | | | | Mean of Synergy Score | Synergy Score Error (sd) | Mean of Synergy Score | Synergy Score Error (sd) |
| MV4; 11 | 0.1 | 0.3 | 5.0 | 4.1 | 1.9 | 8.1 | 1.6 |
| MOLM-13 | 0.1 | 0.3 | 5.0 | 4.8 | 1.0 | 5.4 | 1.3 |
| PL-21 | 0.3 | 2.0 | 5.0 | 1.5 | 0.2 | 1.6 | 0.1 |

TABLE 5-continued

Synergy scores for Mcl-1 inhibitors in combination with decitabine in the indicated AML cell lines. Interactions were deemed synergistic when scores ≥2.0 where observed. Start concentrations of compounds, mean of max inhibition and the standard deviation (sd) of the synergy scores are indicated.

| Cell Line | Compound 1 Start conc [µM] | Compound 2 Start conc [µM] | Decitabine Start conc [µM] | Combination Compound 1 + Decitabine | | Combination Compound 2 + Decitabine | |
|---|---|---|---|---|---|---|---|
| | | | | Mean of Synergy Score | Synergy Score Error (sd) | Mean of Synergy Score | Synergy Score Error (sd) |
| ML-2 | 0.1 | 0.3 | 5.0 | 4.3 | 0.4 | 3.7 | 0.7 |
| Nomo-1 | — | 0.3 | 5.0 | ND | ND | 4.1 | 1.0 |
| THP-1 | — | 0.3 | 5.0 | ND | ND | 1.7 | 0.4 |
| HL-60 | — | 0.3 | 5.0 | ND | ND | 2.3 | 0.2 |
| Kasumi-1 | — | 0.3 | 5.0 | ND | ND | 4.8 | 0.4 |
| OCI-AML3 | 2 | 2.0 | 5.0 | 6.6 | 0.7 | 7.1 | 0.0 |
| EOL-1 | — | 0.1 | 5.0 | ND | ND | 6.3 | 1.2 |
| GDM-1 | 0.1 | 0.3 | 5.0 | 4.5 | 0.3 | 4.3 | 0.6 |
| KG1 | — | 2.0 | 5.0 | ND | ND | 2.8 | 0.4 |
| KG1a | — | 5.0 | 5.0 | ND | ND | 2.7 | 0.8 |

Results

The effect on proliferation of combining the Mcl1 inhibitors of the invention with cytarabine, idarubicin and decitabine was assessed in a panel of 13 AML cell lines. Mcl-1 inhibitors as single agents strongly inhibited the growth of the majority of the 13 AML lines tested ($IC_{50}$ values from 1 nM to 2.2 µM—Table 2). In combination with the standard-of-care drugs cytarabine, idarubicin and decitabine, synergistic growth inhibition (i.e. Synergy Scores above 2 (Lehar et al, 2009)) for the majority of the cell lines tested was observed (Tables 3, 4 and 5). These data indicate that the combination of Mcl-1 inhibitors with the standard-of-care drugs for the treatment of hematologic cancer could provide benefit to the treatment of AML patients.

Example 2: Synergistic Pro-Apoptotic Activity of Combining MCL-1 Inhibitors with Idarubicin in Primary Human AML Samples Material and Method: Patient AML Cells Bone marrow samples from patients with AML were collected after informed consent in accordance with guidelines approved by The Alfred Hospital Human research ethics committee.

Mononuclear cells were isolated by density-gradient centrifugation Ficoll-Hypaque (GE Healthcare, Australia) density-gradient centrifugation and red cell lysis was performed using 0.156 M $NH_4Cl$, 0.017 M Tris-HCl pH 7.2 as previously described (Rijal et al., Blood 2015, 125, 2815-2824). Cells were then re-suspended in phosphate-buffered saline containing 2% Fetal Bovine serum (FBS; Sigma, Australia). Mononuclear cells were then suspended in RPMI-1640 (GIBCO, Australia) medium containing penicillin and streptomycin (GIBCO) and heat inactivated fetal bovine serum 15% (Sigma). Cells were washed in phosphate-buffered saline (PBS) containing 2% FBS prior to use.

Cell Viability Assays

Freshly purified mononuclear cells from AML patient samples were adjusted to a concentration of $2.5 \times 10^5$/mL and 100 µL of cells aliquoted per well into 96 well plates (Sigma). Cells were then treated with idarubicin and Compound 2 over a 5 log concentration range from 1 nM to 10 µM for 48 hours. For combinations assays, drugs were added at a 1:1 ratio from 1 nM to 10 µM and cells were incubated at 37° C. 5% $CO_2$. Cells were then stained with Sytox blue nucleic acid stain (Invitrogen, Australia) and fluorescence measured by flow cytometric analysis using the LSR-II Fortessa (Becton Dickinson, Australia). FACSDiva software was used for data collection, and FlowJo software for analysis. Blast cells were gated using forward and side scatter properties. Viable cells excluding Sytox blue were determined at 6 concentrations for each drug and the 50% lethal concentration ($LC_{50}$, in µM) determined.

TABLE 6

Synergistic pro-apoptotic activity in primary human AML samples.

| Patient AML | Compound 2 (µM) | Idarubicin (µM) | Compound 2 + Idarubicin (µM) |
|---|---|---|---|
| AH6214498 | 0.0008676 | 0.001114 | 0.0004251 |
| AH6223646 | 0.1476 | 0.3153 | 0.0008576 |
| AH6607085 | 0.1427 | 0.563 | 0.0009918 |
| AH6229985 | 0.004826 | 0.001379 | 0.001667 |
| AH0979006 | 0.06177 | 0.001069 | 0.004134 |
| AH6220847 | 0.2097 | 0.01442 | 0.004207 |
| AH6208654 | 9.424 | 0.308 | 0.004915 |
| 6200840 | 0.2268 | 0.3844 | 0.006903 |
| AH6210946 | 0.0556 | 0.1054 | 0.01187 |
| AH6217528 | 1.157 | 0.03348 | 0.02817 |
| AH1081582 | 4.355 | 0.1839 | 0.08559 |
| AH0131936 | 10.65 | 0.8862 | 0.09514 |
| AH0607688 | 22.87 | 0.5928 | 0.5928 |
| AH6208160 | 21.62 | 1.75 | 0.6885 |
| AH6627892 | 14.16 | 2.204 | 0.936 |
| AH6202849 | 13.01 | 2.874 | 1.145 |
| AH6181414_2 | 15.5 | 3.468 | 1.703 |
| AH6615742 | 14.51 | 2.934 | 2.932 |
| AH0465385 | 23.02 | 5.128 | 4.969 |
| AH6120264 | 0.6793 | 0.328 | 5.077 |
| AH6219953 | 38.83 | 4.367 | 6.111 |
| AH1228742 | 5365 | 404 | 90.68 |
| AH6224104 | 607.8 | 192.3 | 192.3 |

Results

Figure 2:
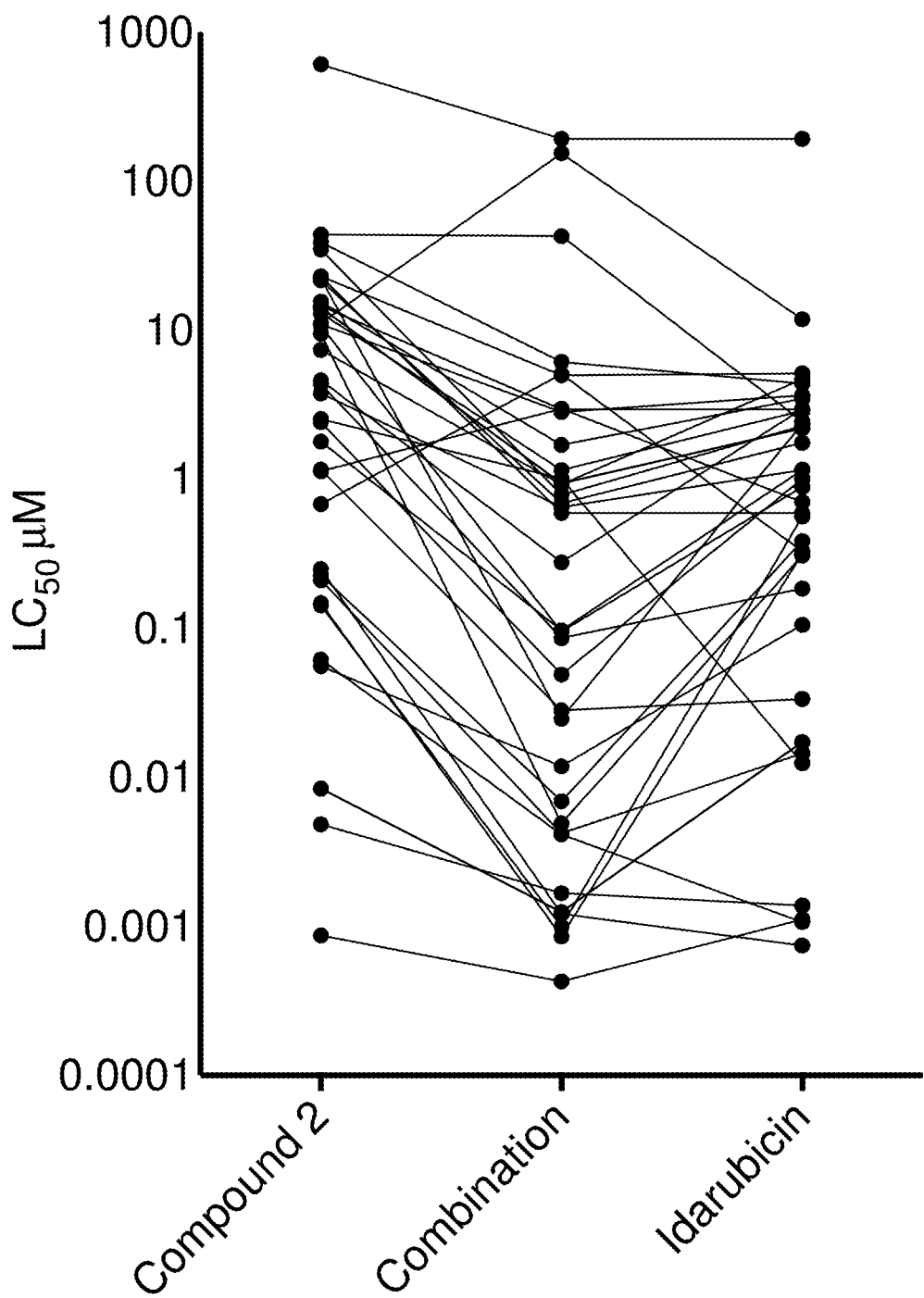
FIG. 2 illustrates that combination of a Mcl-1 inhibitor with idarubicin has synergistic activity in AML. A series of primary AML samples from patients with diverse cytogenetic and molecular characteristics were incubated for 48 hours with Compound 2 or idarubicin alone, or in combination and the LC$_{50}$ killing effect determined. This showed substantial synergy of this combination in a large proportion of primary AML samples.

The effect on survival of combining the Mcl-1 inhibitors of the invention with idarubicin was assessed in several primary human AML samples (FIG. 2; Table 6). Even if several samples are sensitive to Mcl-1 inhibitors and standard-of-care drugs for the treatment of AML as monotherapy, a larger number of samples wherein the monotherapy is ineffective or poorly effective are synergistically sensitive to the combination of Mcl-1 inhibitors with standard-of-care drugs for the treatment of hematologic cancer showing that the combination could provide benefit to the treatment of AML patients.

Example 3: Leukemic Blasts Displayed Greater Sensitivity to Mcl-1 Inhibitors Combined with Cytarabine than CD34+ Hematopoietic Precursors Material and Method: Colony Assays Colony forming assays were performed on freshly purified and frozen mononuclear fractions from AML patients.

Primary cells were cultured in duplicate in 35 mm dishes (Griener-bio, Germany) at $1\times10^4$ to $1\times10^5$. Cells were plated in 0.6% agar (Difco, Australia): AIMDM 2× (IMDM powder-Invitrogen, supplemented with $NaHCO_3$, dextran, Pen/Strep, B mercaptoethanol and asparagine): Fetal Bovine Serum (Sigma) at a 2:1:1 ratio. For optimal growth conditions all plates contained GM-CSF (100 ng per plate), IL-3 (100 ng/plate R&D Systems, USA), SCF (100 ng/plate R&D Systems) and EPO (4 U/plate). Growth was for 2-3 weeks in the presence and absence of drug at 37° C. at 5% $CO_2$ in a high humidity incubator. After incubation plates were fixed with 2.5% glutaraldehyde in saline and scored using the GelCount from Oxford Optronix (Abingdon, United Kingdom).

Results

Figure 3:
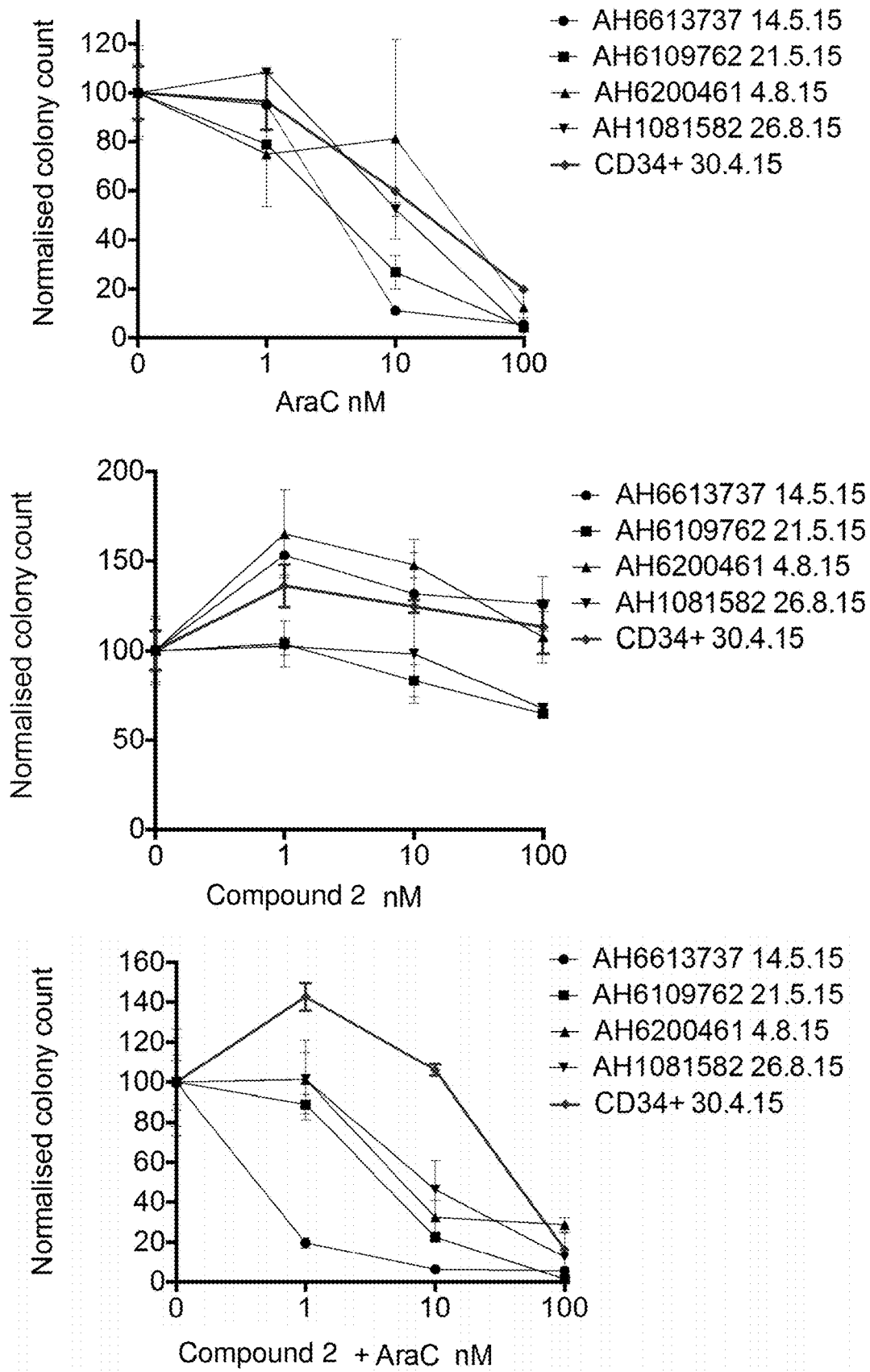
FIG. 3 illustrates a comparison activity against primary AML samples relative to healthy CD34+ donor cells for cytarabine, Compound 2 (Mcl-1 inhibitor) and Compound 2 in combination with cytarabine. The viability of primary AML cells and normal CD34+ cells (grey line) normalized to vehicle control after exposure to cytarabine, Compound 2 and Compound 2 in combination with cytarabine (in nM) are shown.

In clonogenic assays, a subset of primary AML samples and normal human CD34+ progenitor cells were resistant to 100 nM Compound 2. By contrast, the standard-of-care drugs, such as cytarabine 10 nM, were toxic to clonogenic growth of both leukemic and normal progenitor cells. Finally, a subset of primary AML samples was sensitive to 10 nM Compound 2+cytarabine, whereas normal human CD34+ progenitor cells were less affected by this dose (FIG. 3).

Example 4: Mcl-1 Inhibitor Combined with Decitabine is Well Tolerated In Vivo

To determine the tolerability of Compound 2 in combination with decitabine, NSG mice were treated with:
a) decitabine 0.4 mg/kg or 0.8 mg/kg IP injection, or
b) decitabine 0.4 mg/kg or 0.8 mg/kg in combination with Compound 2 25 mg/kg (IV), over 1 week and white blood cells (WBC), platelet, hemoglobin (Hb), red blood cells (RBC) counts were determined using the Hemavet blood analyzer.

Figure 4:
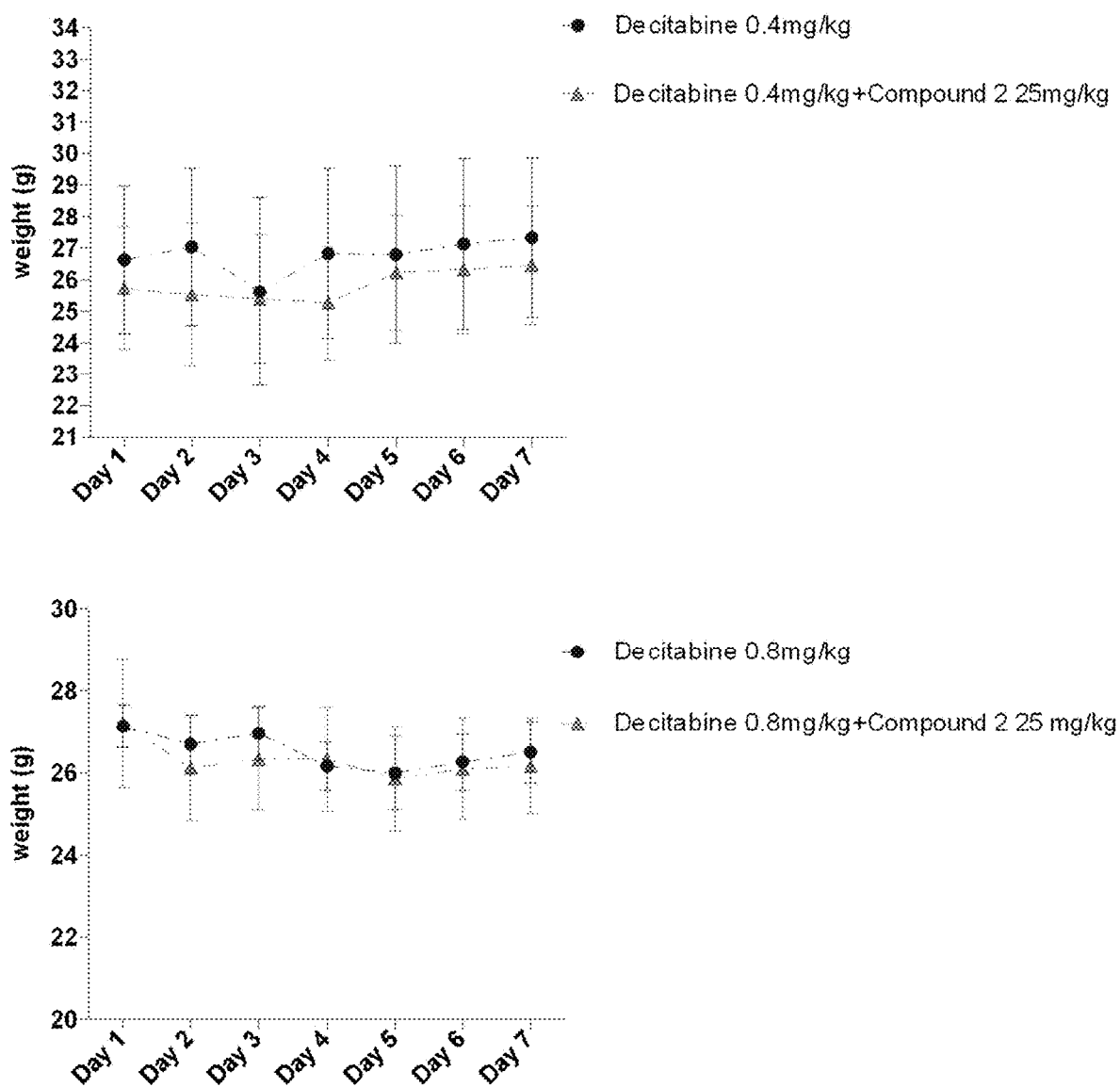
FIG. 4 illustrates the maintaining of normal body weight during therapy. NSG mice were treated with decitabine 0.4 mg/kg or 0.8 mg/kg IP injection or decitabine 0.4 mg/kg or 0.8 mg/kg in combination with Compound 2 (Mcl-1 inhibitor) 25 mg/kg (IV) over 1 week.
Figure 5:
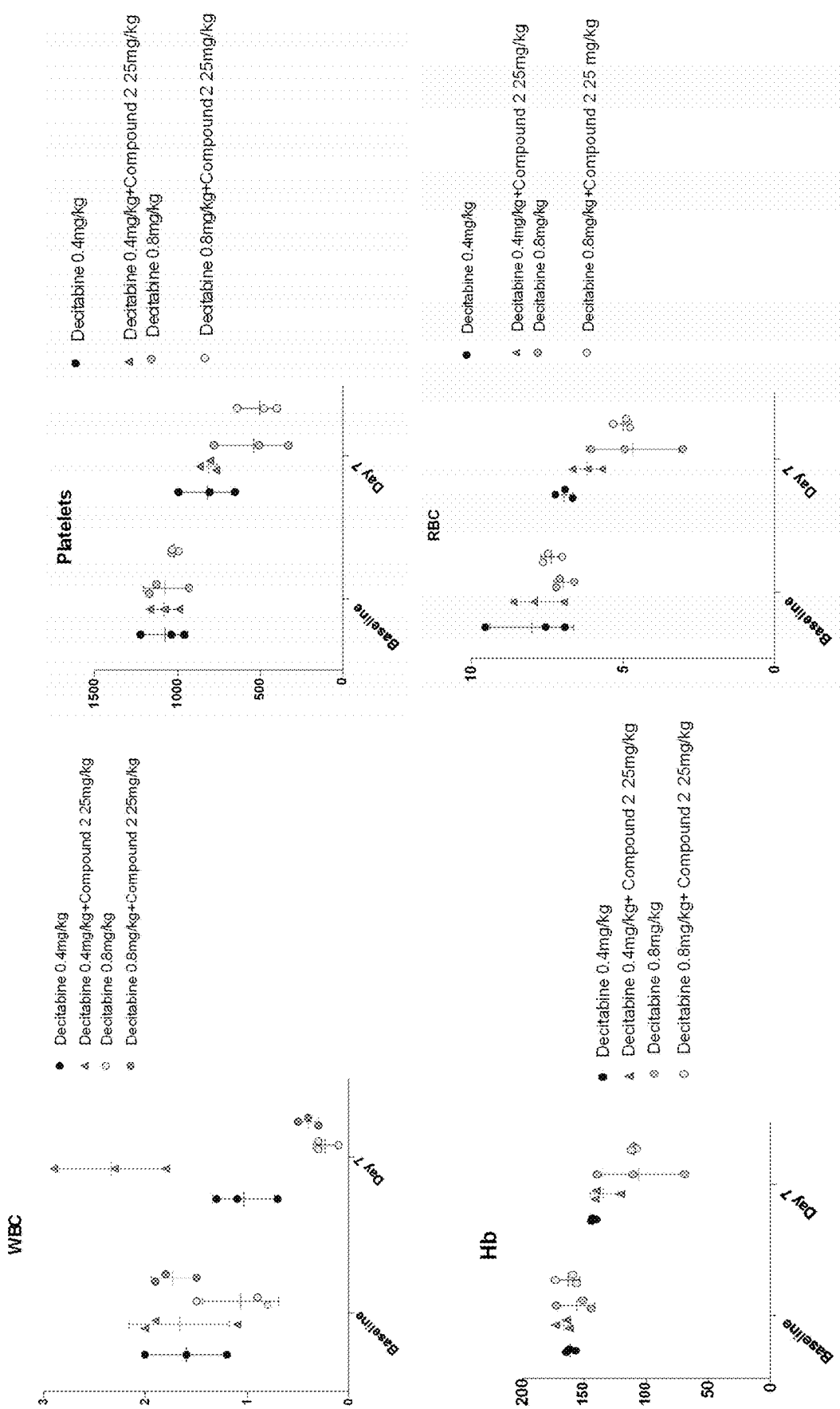
FIG. 5 illustrates the hematologic toxicity in NSG mice during therapy. NSG mice were treated with decitabine 0.4 mg/kg or 0.8 mg/kg IP injection or decitabine 0.4 mg/kg or 0.8 mg/kg in combination with Compound 2 (Mcl-1 inhibitor) 25 mg/kg (IV) over 1 week and white blood cells (WBC), platelet, hemoglobin (Hb), red blood cells (RBC) counts determined using the Hemavet blood analyzer.

Compound 2 combined with decitabine was well-tolerated (FIG. 5) and mice did not lose weight during treatment (FIG. 4).

Taken altogether, Examples 2, 3 and 4 show that the combination of a Mcl-1 inhibitor and a standard-of-care drug for the treatment of hematologic cancer is a novel approach to treating in particular AML, without need for additional chemotherapy and with an acceptable therapeutic safety window.

Example 5: Mcl-1 Inhibitor Combined with Decitabine Synergistically Inhibits PDX AML In Vivo Material and Method Bone marrow leukemic blasts from AML patient sample AML54 were intravenously injected into NOD-IL2Rγcnull (NRG) mice (The Jackson Laboratory, Bar Harbor, USA) for expansion. The NRG-SG3 mice were monitored for leukemia development by flow cytometric analysis of peripheral blood for human CD45-positive (hCD45+) cells. To establish mouse models of patient primary AML, $1\times10^6$ leukemic blasts were injected into NRG-SG3 mice via tail-vein injection and animals monitored for leukemia progression using flow cytometric analysis of peripheral blood for hCD45+ cells. hCD45+ cell counts in the bone marrow from the femurs of euthanized animals were used to determine the extent of leukemia infiltration. Bone marrow cells were extracted by flushing femurs in PBS supplemented with 2% fetal bovine serum. To determine efficacy on AML, cohorts of mice were treated with vehicle control, decitabine (0.4 mg/kg) daily IP for 5 days, twice weekly IV injection with Compound 2 (Mcl-1 inhibitor, 25 mg/kg) or decitabine in combination with Compound 2. Drug efficacy was determined by flow cytometric analysis of hCD45+ cells in bone marrow isolated from femurs of mice in vehicle.

Results

As shown in FIG. 6, there was a remarkable decrease in human AML cell numbers in mice treated by decitabine in combination with Compound 2, with hCD45+ cells accounting for less than 9% of bone marrow leukocytes. These results indicate that combination of a Mcl-1 inhibitor and a standard-of-care drug for the treatment of hematologic cancer effectively kills the bulk human AML blast cells in the PDX model of AML54.

Example 6: Synergistic Pro-Apoptotic Activity of Combining MCL-1 Inhibitors with Standard-of-Care Drugs in Primary Human ALL Samples Material and Method: Primary ALL Patient Samples Bone marrow or peripheral blood samples from patients with ALL were collected after informed consent in accordance with guidelines approved by The Alfred Hospital Human research ethics committee. Mononuclear cells were isolated by Ficoll-Paque (GE Healthcare, Australia) density-gradient centrifugation, followed by red cell depletion in ammonium chloride ($NH_4Cl$) lysis buffer at 37° C. for 10 minutes. Cells were then re-suspended in phosphate-buffered saline containing 2% Fetal Bovine serum (Sigma, Australia). Mononuclear cells were then suspended in RPMI-1640 (GIBCO, Australia) medium containing penicillin and streptomycin (GIBCO) and heat inactivated fetal bovine serum 15% (Sigma).

Cell Viability

Freshly purified mononuclear cells from ALL patient samples were adjusted to a concentration of $2.5\times10^5$/ml and 100 µL of cells aliquoted per well into 96 well plates (Sigma). Cells were then treated with indicated drugs over a 6 log concentration range from 1 nM to 10 µM for 48 hours. For combinations assays, drugs were added at a 1:1 ratio from 1 nM to 10 µM and incubated at 37° C. 5% $CO_2$. Cells were then stained with sytox blue nucleic acid stain (Invitrogen, Australia) and fluorescence measured by flow cytometric analysis using the LSR-II Fortessa (Becton Dickinson, Australia). FACSDiva software was used for data collection, and FlowJo software for analysis. Blast cells were gated using forward and side scatter properties. Viable cells excluding sytox blue were determined at 6 concentrations for each drug and the 50% lethal concentration ($LC_{50}$, in µM) determined.

TABLE 7

Synergistic pro-apoptotic activity in primary human ALL samples.

| Patient AML | Compound 2 (µM) | Cytarabine (µM) | Compound 2 + Cytarabine (µM) |
|---|---|---|---|
| AH6198549 | 0.0159 | 10,62 | 0.0131 |
| AH7024700 | 1.31 | 35.89 | 0.0283 |
| AH7008157 | 0.0129 | >100 | 0.0144 |
| TB 17-06-18 | 8.489 | >100 | 0.0718 |
| TB 15-06-05 | 0.9755 | >100 | 0.4898 |
| TB 10-05-02 | >10 | >100 | 33.69 |
| TB 11-08-06 | >10 | >100 | 0.2241 |
| AH6258921 | 2.959 | >100 | 10.34 |
| AH6196680 | 1.061 | >100 | 1.834 |
| TB120803 | 2.143 | >100 | 7.803 |
| AH7104727 | 3.213 | >100 | 22.55 |
| AH6031524 | 7.048 | 51.65 | >10 |
| AH6184311 | 4.882 | 87.96 | 10.4 |
| TB151005 | >10 | >100 | >100 |
| 01-046-2018 | 1.301 | >100 | 2.837 |

Results

The effect on survival of combining the Mcl-1 inhibitors of the invention with cytarabine was assessed in several primary human ALL samples (Table 7). Even if several samples are sensitive to Mcl-1 inhibitors and standard-of-care drugs for the treatment of ALL as monotherapy, a larger number of samples wherein the monotherapy is ineffective or poorly effective are synergistically sensitive to the combination of Mcl-1 inhibitors with standard-of-care drugs for the treatment of hematologic cancer showing that the combination could provide benefit to the treatment of ALL patients.

Example 7: Mcl-1 Inhibitor Combined with Decitabine Synergistically Inhibits PDX AML In Vivo Material and Method To establish mouse models of primary patient AML, 1×10$^6$ leukemic blasts were injected into NOD-IL2Rcγ$^{null}$ (NRG-SG3) mice (The Jackson Laboratory, Bar Harbor, Me., USA) via tail-vein injection and animals monitored for leukemia progression using flow cytometric analysis of peripheral blood for hCD45+ cells. hCD45+ cell counts in the bone marrow from the femurs of euthanized animals were used to determine the extent of leukemia infiltration. Bone marrow cells were extracted by flushing femurs in PBS supplemented with 2% fetal bovine serum. To determine the efficacy of Compound 1 plus decitabine, mice received Compound 1 25 mg/kg twice weekly IV and decitabine IP daily (D1-D5) 0.4 mg/kg. Drug efficacy was determined by flow cytometric analysis of hCD45+ cells in bone marrow isolated from flushed femurs. Sternums were fixed in formalin, sectioned and stained with hematoxylin and eosin or anti-hCD45 to assess leukemic burden and cellularity.

Results

The results obtained show that the combination of Mcl-1 inhibitors with standard-of-care drugs for the treatment of hematologic cancer could provide benefit to the treatment of AML patients.

The invention claimed is:

1. A combination comprising:
   (a) a Mcl-1 inhibitor selected from (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[1-(2,2,2-trifluoroethyl)-1H-pyrazol-5-yl]methoxy}phenyl)propanoic acid, its enantiomers, diastereoisomers, atropisomers, and addition salts thereof with a pharmaceutically acceptable acid or base; and (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl) propanoic acid, its enantiomers, diastereoisomers, atropisomers, and addition salts thereof with a pharmaceutically acceptable acid or base, and (b) second anticancer agent, wherein the second anticancer agent is idarubicin; cytarabine or a hypomethylating agent selected from decitabine and azacitidine.

2. The combination according to claim 1, wherein the second anticancer agent is idarubicin.

3. The combination according to claim 1, wherein the second anticancer agent is cytarabine.

4. The combination according to claim 1, wherein the second anticancer agent is decitabine.

5. The combination according to claim 1, wherein the second anticancer agent is azacitidine.

6. The combination according to claim 1, wherein the Mcl-1 inhibitor is (2R)-2-{[(5S$_a$)-5-{3-chloro-2-methyl-4-[2-(4-methylpiperazin-1-yl)ethoxy]phenyl}-6-(5-fluorofuran-2-yl)thieno[2,3-d]pyrimidin-4-yl]oxy}-3-(2-{[1-(2,2,2-trifluoroethyl)-1H-pyrazol-5-yl]methoxy}phenyl) propanoic acid.

7. The combination according to claim 1, wherein the Mcl-1 inhibitor is (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid.

8. The combination according to claim 7, wherein the (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid is present at a dosage from 25 mg to 1500 mg.

9. combination according to claim 1, further comprising one or more excipients.

10. The combinationon according to claim 1, further comprising a third anticancer agent.

11. The combination according to claim 10, wherein the third cancer agent is idarubicin.

12. A pharmaceutical composition comprising the combination according to claim 1 in combination with one or more pharmaceutically acceptable excipients.

13. The pharmaceutical composition according to claim 12 which is packaged for simultaneous, sequential or separate administration.

14. A method of treating cancer in a subject in need thereof, comprising administration of an effective amount of the combination according to claim 1, alone or in combination with one or more pharmaceutically acceptable excipients.

15. The method according to claim 14, wherein the Mcl-1 inhibitor is administered orally.

16. The method according to claim 14, wherein the Mcl-1 inhibitor is administered intravenously.

17. The method according to claim 14, wherein the cancer is acute myeloid leukemia or acute lymphocytic leukemia.

18. The method according to claim 14, wherein the Mcl-1 inhibitor and the second anticancer agent are provided in amounts which are jointly therapeutically effective for the treatment of cancer.

19. The method according to claim 14, wherein the Mcl-1 inhibitor and the second anticancer agent are provided in amounts which are synergistically effective for the treatment of cancer.

20. The method according to claim 14, wherein the Mcl-1 inhibitor and the second anticancer agent are provided in synergistically effective amounts which enable a reduction of the dose required for each compound in the treatment of cancer, whilst providing an efficacious cancer treatment, with eventually a reduction in side effects.

21. The method according to claim 17, wherein treatment is carried out in patients having acute myeloid leukemia who have achieved remission.

22. The method according to claim 14, wherein the Mcl-1 inhibitor is (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid.

23. The method according to claim 22, wherein the (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid is administered once a week.

24. A method for sensitizing a patient who is (i) refractory to at least one chemotherapy treatment, or (ii) in relapse after treatment with chemotherapy, or both (i) and (ii), wherein the method comprises administering a therapeutically effective amount of:
the combination according to claim 1 to said patient, wherein said patient is responsive to the treatment comprising administration of the combination or said patient does not develop resistance to the treatment comprising administration of the combination.

25. The method according to claim 24, wherein the Mcl-1 inhibitor is (2R)-2-{[(5S$_a$)-5-{3-chloro-2-methyl-4-[2-(4-methylpiperazin-1-yl)ethoxy]phenyl}-6-(4-fluorophenyl)thieno[2,3-d]pyrimidin-4-yl]oxy}-3-(2-{[2-(2-methoxyphenyl)pyrimidin-4-yl]methoxy}phenyl)propanoic acid.

* * * * *

UNITED STATES PATENT AND TRADEMARK OFFICE
CERTIFICATE OF CORRECTION

Page 1 of 1

PATENT NO. : 11,466,023 B2
APPLICATION NO. : 16/622967
DATED : October 11, 2022
INVENTOR(S) : Andrew Wei et al.

It is certified that error appears in the above-identified patent and that said Letters Patent is hereby corrected as shown below:

In the Claims

Claim 1, Column 33, Line 65: "(a) a" should read -- (a) an --.
Column 34, Line 13: "(b)" should read -- (b) a --.

Claim 9, Column 34, Line 44: Insert -- The -- before "combination".

Signed and Sealed this
Sixth Day of December, 2022

Katherine Kelly Vidal
*Director of the United States Patent and Trademark Office*